United States Patent
Schonbrunn et al.

(10) Patent No.: US 9,808,447 B2
(45) Date of Patent: Nov. 7, 2017

(54) INHIBITORS OF RHO ASSOCIATED PROTEIN KINASES (ROCK) AND METHODS OF USE

(71) Applicant: H. Lee Moffitt Cancer Center and Research Institute, Inc., Tampa, FL (US)

(72) Inventors: Ernst Schonbrunn, Tampa, FL (US); Rongshi Li, Omaha, NE (US); Said M. Sebti, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 15/231,124

(22) Filed: Aug. 8, 2016

(65) Prior Publication Data

US 2017/0049760 A1    Feb. 23, 2017

Related U.S. Application Data

(63) Continuation of application No. 14/374,445, filed as application No. PCT/US2013/022965 on Jan. 24, 2013, now Pat. No. 9,409,868.

(60) Provisional application No. 61/590,283, filed on Jan. 24, 2012, provisional application No. 61/590,573, filed on Jan. 25, 2012.

(51) Int. Cl.
| | |
|---|---|
| *A61K 31/4418* | (2006.01) |
| *A61K 31/416* | (2006.01) |
| *A61K 31/4409* | (2006.01) |
| *A61K 31/4439* | (2006.01) |
| *A61K 31/551* | (2006.01) |
| *C07D 231/56* | (2006.01) |
| *C07D 213/40* | (2006.01) |
| *A61K 45/06* | (2006.01) |
| *A61N 5/10* | (2006.01) |
| *C07D 213/36* | (2006.01) |

(52) U.S. Cl.
CPC ........ *A61K 31/4418* (2013.01); *A61K 31/416* (2013.01); *A61K 31/4409* (2013.01); *A61K 31/4439* (2013.01); *A61K 31/551* (2013.01); *A61K 45/06* (2013.01); *A61N 5/10* (2013.01); *C07D 213/36* (2013.01); *C07D 213/40* (2013.01); *C07D 231/56* (2013.01)

(58) Field of Classification Search
None
See application file for complete search history.

(56) References Cited

U.S. PATENT DOCUMENTS

| | | | |
|---|---|---|---|
| 6,960,648 | B2 | 11/2005 | Bonny |
| 2002/0035243 | A1 | 3/2002 | Imfeld et al. |
| 2002/0120100 | A1 | 8/2002 | Bonny |
| 2002/0173507 | A1 | 11/2002 | Santora et al. |
| 2003/0032594 | A1 | 2/2003 | Bonny |

FOREIGN PATENT DOCUMENTS

| | | |
|---|---|---|
| WO | 2004064730 | 8/2004 |
| WO | 2010036316 | 4/2010 |

OTHER PUBLICATIONS

Austin, et al., NIH Molecular Libraries Initiative, Science, 306:1138-1139, 2004.
Bosanac, et al., Substituted 2H-isoquinolin-1-ones as potent Rho-kinase inhibitors: Part 3, aryl substituted pyrrolidines, Bioorg. Med. Chem. Lett., 20:3746-3749. 2010.
Brittain, et al. "Polymorphism in Pharmaceutical Solids," NY: Marcel Dekker, Inc., 1999, 1-2, 125-181, 183-226.
Chang, et al., Activation of Rho-associated coiled-coil protein kinase 1 (ROCK-1) by caspase-3 cleavage plays an essential role in cardiac myocyte apoptosis, Proc Natl Acad Sci USA, 103:14495-14500, 2006.
Chen, et al., Chroman-3-amides as potent Rho kinase inhibitors, Bioorg Med Chem Lett, 18:6406-6409, 2006.
Coleman, et al., Membrane blebbing during apoptosis results from caspase-mediated activation of ROCK I, Nat Cell Biol, 3:339-45, 2001.
Database Registry Chemical Abstracts Service, Columbus, Ohio, Accession No. RN 1055941-86-0, Entered STN: Oct. 1, 2008.
Dong, et al., Current Status of Rho-Associated Kinases (ROCKs) in Coronary Atherosclerosis and Vasospasm, Cardiovasc Hematol Agents Med Chem, 7:322-330, 2009.
Fang, et al., Synthesis and biological evaluation of 4-quinazolinones as Rho kinase inhibitors, Bioorg Med Chem Lett, 21:1844-1848, 2011.
Feng, et al., Discovery of Substituted 4-(Pyrazol-4-yl)-phenylbenzodioxane-2-carboxamides as Potent and Highly Selective Rho Kinase (Rock-II) Inhibitors, J Med Chem, 51:6642-6645, 2008.
Friesner, et al., Glide: A New Approach for Rapid, Accurate Docking and Scoring. 1. Method and Assessment of Docking Accuracy, J Med Chem, 47:1739-1749, 2004.
Ginn, et al., Substituted 2H-isoquinolin-1-ones as potent Rho-kinase inhibitors: Part 2, optimization for blood pressure reduction in spontaneously hypertensive rats, Bioorg Med Chem Lett, 20:5153-5156, 2010.
Gishi, el al., Enhancement of cisplatin-induced cytotoxicity by ROCK inhibitor through suppression of focal adhesion kinase independent mechanism in lung carcinoma cells, Int J Oncol, 23:1079-1085, 2003.
Goodman, et al., Development of Dihydropyridone Indazole Amides as Selective Rho-Kinase Inhibitors, J Med Chem, 50:6-9, 2007.

(Continued)

*Primary Examiner* — Samantha Shterengarts
(74) *Attorney, Agent, or Firm* — Meunier Carlin & Curfman LLC

(57) ABSTRACT

Compounds and compositions having activity as inhibitors of Rho-associated proteinkinases (ROCKs), and methods of making and using the subject compounds are disclosed.

21 Claims, 6 Drawing Sheets

(56) References Cited

OTHER PUBLICATIONS

Halgren, et al., Glide: A New Approach for Rapid, Accurate Docking and Scoring. 2. Enrichment Factors in Database Screening, J Med Chem, 47:1750-1759, 2004.
Hampson, et al., Analogues of Y27632 increase gap junction communication and suppress the formation of transformed NIH3T3 colonies, Br J Cancer, 101:829-839, 2009.
Henderson, et al., 2,3-Diaminopyrazines as rho kinase inhibitors, Bioorg Med Chem Lett, 20:1137-1140, 2010.
Ho, et al., Triazine and pyrimidine based ROCK inhibitors with efficacy in spontaneous hypertensive rat model, Bioorg Med Chem Lett, 19:6027-6031, 2009.
Huryn, et al., The Molecular Libraries Screening Center Network (MLSCN): Identifying Chemical Probes of Biological Systems, Ann Rep Med Chem, 42:401-416, 2007.
Imamura, et al., Y-27632, an Inhibitor of Rho-associated Protein Kinase, Suppresses Tumor Cell Invasion via Regulation of Focal Adhesion and Focal Adhesion Kinase, Jpn J Cancer Res, 91:811-816, 2000.
International Search Report and Written Opinion for PCT/2013/022965, dated May 9, 2013.
Ishizaki, et al., Pharmacological Properties of Y-27632, a Specific Inhibitor of Rho-Associated Kinases, Mol Pharmacol, 57:976-983, 2000.
Itoh, et al. An essential part for Rho-associated kinase in the transcellular invasion of tumor cells, Nat Med (NY), 5:221-225, 1999.
Iwakubo, et al., Design and synthesis of rho kinase inhibitors (III), Bioorg Med Chem, 15:1022-1033, 2007.
Iwakubo, et al., Design and synthesis of Rho kinase inhibitors (II), Bioorg Med Chem, 15:350-364, 2007.
Jacobs, et al., The Structure of Dimeric ROCK I Reveals the Mechanism for Ligand Selectivity, J Biol Chem, 281:260-268, 2006.
Kamai, et al. Overexpression of RhoA, Rac1, and Cdc42 GTPases Is Associated with Progressionin Testicular Cancer, Clinical Cancer Res, 10:4799-4805, 2004.
Kang, et al., Identification of small molecules that inhibit GSK-3b through virtual screening, Bioorg Med Chem Left, 19:533-537, 2009.
Kazi, et al., Blockade of Protein Geranylgeranylation Inhibits Cdk2-Dependent p27Kip1 Phosphorylation on Thr187 and Accumulates p27Kip1 in the Nucleus: Implications for Breast Cancer Therapy, Mol Cell Biol, 29:2254-2263, 2009.
Koresawa, et al., High-Throughput Screening with Quantitation of ATP Consumption: A Universal Non-Radioisotope, Homogeneous Assay for Protein Kinase, Assay Drug Dev Technol, 2:153-160, 2004.
Kubo, et al., Rho-ROCK Inhibitors for the Treatment of CNS Injury, Recent Pat CNS Drug Discov, 2:173-179, 2007.
Kubo, et al., The therapeutic effects of Rho-ROCK inhibitors on CNS disorders, Ther Clin Risk A1anage, 4:605-615, 2008.
Liao, et al., Rho Kinase (ROCK) Inhibitors, J 30 Cardiovasc Pharmacal, 50:17-24, 2007.
Liu, et al., Inhibition of Rho-Associated Kinase Signaling Prevents Breast Cancer Metastasis to Human Bone, Cancer Res, 69:87 4 2-87 51, 2009.
Lograsso, et al., Rho Kinase (ROCK) Inhibitors and Their Application to Inflammatory Disorders, Curr Top Med Chem, 9:704-23, 2009.
Morwick, et al., Hit to Lead Account of the Discovery of Bisbenzamide and Related Ureidobenzamide Inhibitors of Rho Kinase, Med. Chem., 53:759-777, 2009.
Nakagawa, et al., ROCK-I and ROCK-II, two isoforms of Rho-associated coiled-coil forming protein serine/threonine kinase in mice, FEBS Lett, 392:189-193, 1996.
Nakajima, et al., Effect of Wf-536, a novel ROCK inhibitor, against metastasis of B16 melanoma, Cancer Chemother Pharmacol, 52:319-24, 2003a.
Nakajima, et al., Wf-536 prevents tumor metastasis by inhibiting both tumor motility and angiogenic actions, Eur J Pharmacol, 459:113-20, 2003b.
Narumiya, et al., [24] Use and Properties of ROCK-Specific Inhibitor Y-27632, Methods Enzymol, 325:273-84, 2000.
Ogata, et al., Fasudil Inhibits Lysophosphatidic Acid- Induced Invasiveness of Human Ovarian Cancer Cells, Int J Gynecol Cancer, 19:1473-80, 2009.
Ray, Jet al., Fragment-based discovery of 6-substituted isoquinolin-1-amine based ROCK-I inhibitors, Bioorg Med Chem Lett, 21:97-101, 2011.
Ray, et al., Optimisation of 6-substituted isoquinolin-1-amine based ROCK-I inhibitors, Bioorg Med Chem Lett, 21:1084-1088, 2011.
Rikitake, et al., Decreased Perivascular Fibrosis but Not Cardiac Hypertrophy in ROCK1+/− Haploinsufficient Mice, Circulation, 112:2959-2965, 2005.
Sapet, et al., Thrombin-induced endothelial microparticle generation: identification of a novel pathway involving ROCK-II activation by caspase-2, Blood, 108:1868-1876, 2006.
Schmitz, et al., Rho GTPases: Signaling, Migration, and Ivasion, Exp Cell Res, 261:1-12, 2000.
Sebbagh, et al., Caspase-3-mediated cleavage of ROCK I induces MLC phosphorylation and apoptotic membrane blebbing, Nat Cell Biol, 3:346-352, 2001.
Sebbagh, et al., Direct cleavage of ROCK II by granzyme B induces target cell membrane blebbing in a caspase-independent manner, J Exp Med., 201:465-471, 2005.
Sehon, et al., Potent, Selective and Orally Bioavailable Dihydropyrimidine Inhibitors of Rho Kinase (ROCK1) as Potential Therapeutic Agents for Cardiovascular Diseases, J Med Chem, 51:6631-6634, 2008.
Sessions, et al., Benzimidazole- and benzoxazole-based inhibitors of Rho kinase, Bioorg Med Chem Left, 18:6390-6393, 2008.
Shimizu, et al. ROCK-I regulates closure of the eyelids and ventral body wall by inducing assembly of actomyosin bundles, J Cell Biol, 168:941-53, 2005.
Shimokawa, et al., Rho-Kinase Is an Important Therapeutic Target in Cardiovascular Medicine, Arterioscler Thromb Vase Biol, 25:1767-1775, 2005.
Shimokawa, et al., Development of Rho-kinase inhibitors for cardiovascular medicine, Trends Pharmacol Sci, 28:296-302, 2007.
Somlyo, et al., Rho-Kinase Inhibitor Retards Migration and in Vivo Dissemination of Human Prostate Cancer Cells, Biochem Biophys Res Commun, 269:652-659, 2000.
Somlyo, et al., Rho kinase and matrix metalloproteinase inhibitors cooperate to inhibit angiogenesis and growth of human prostate cancer xenotransplants, Faseb J, 17:223-234, 2003.
Suwa, et al., Overexpression of the rhoC gene correlates with progression of ductal adenocarcinoma of the pancreas, Br J Cancer, 77:147-152, 1998.
Takami, et al., Design and synthesis of Rho kinase inhibitors (I), Bioorg Med Chem, 12:2115-2137, 2004.
Thomas, et al., The Pilot Phase of the NIH Chemical Genomics Center, Curr Top. Med Chem, 9:1184-1193, 2009.
Toyoizumi, et al., Combined therapy with chemotherapeutic agents and herpes simplex virus type IICP34.5 mutant (HSV-1716) in human non-small cell lung cancer, Human Gene Therapy, 10(18):17, 1999.
Uchida, et al., The Suppression of Small GTPase Rho Signal Transduction Pathway Inhibits Angiogenesis in Vitro and in Vivo, Biochem Biophys Res Commun, 269:633-640, 2000.
Uehata, et al., Calciumsensitization of smooth muscle mediated by a Rho-associated protein kinase in hypertension, Nature, 389:990-4, 1997.
Vippagunta et al., "Crystalline Solids," Adv Drug Delivery Rev, 48:3-26, 2000.
Xing, et al., Rho-kinase as a Potential Therapeutic Target for the Treatment of Pulmonary Hypertension, Drug News Perspect, 19:517-522, 2006.
Yin, et al., Discovery of Potent and Selective Urea-Based ROCK Inhibitors and Their Effects on Intraocular Pressure in Rats, Med. Chem. Lett., 1:175-179, 2010.

(56) References Cited

OTHER PUBLICATIONS

Yin, et al., Benzothiazoles as Rho-associated kinase (ROCK-II) inhibitors, Bioorg Med Chem Lett, 19:6686-6690, 2009.
Ying, et al., The Rho kinase inhibitor fasudil inhibits tumor progression in human and rat tumor models, Mal Cancer Ther, 5:2158-2164, 2006.
Yoshimi, et al., Antinociceptive Effects of AS1892802, a Novel Rho Kinase Inhibitor, in Rat Models of Inflammatory and Noninflammatory Arthritis, J Pharmacol Exp Ther, 334:955-963, 2010.
Yu et al., "Physical characterization of polymorphic drugs: an integrated characterization strategy," PSTT 1(3):118-127, 1998.
Zhang, et al., Targeted deletion of ROCK1 protects the heart against pressure overload by inhibiting reactive fibrosis, Faseb J, 20:916-925, 2006.
Zohrabian, et al., Rho/ROCK and MAPK Signaling Pathways Are Involved in Glioblastoma Cell Migration and Proliferation, Anticancer Res, 29:119-123, 2009.
Office Action from U.S. Appl. No. 13/640,385, dated Jan. 9, 2015.

Chemical structures and *in vitro* IC$_{50}$

RKI-23
ROCK1 inhibition

RKI-24
ROCK2 inhibition

ROCK1 IC$_{50}$:
RKI-23 = 9.07 + 2.52 μM
RKI-24 = 1.69 + 0.17 μM

ROCK2 IC$_{50}$:
RKI-23 = 7.52 + 1.51 μM
RKI-24 = 0.10 + 0.03 μM

RKI-11
ROCK1 inhibition

RKI-18
ROCK2 inhibition

ROCK1 IC$_{50}$:
RKI-11 = 157 ± 34.1 μM
RKI-18 = 0.65 + 0.03 μM

ROCK1 IC$_{50}$:
RKI-11 = 61.8 ± 9.6 μM
RKI-18 = 0.67 ± 0.23 μM

INHIBITORS OF RHO ASSOCIATED PROTEIN KINASES (ROCK) AND METHODS OF USE

CROSS REFERENCE TO RELATED APPLICATIONS

This application is a divisional of U.S. application Ser. No. 14/374,445, filed on Jul. 24, 2014, which is a 371 national phase of International Application PCT/US2013/022965, filed on Jan. 24, 2013, which claims the benefit of priority to U.S. Provisional Applications 61/590,573, filed Jan. 25, 2012, and 61/590,283, filed Jan. 24, 2012, all of which are incorporated in their entities herein by this reference.

ACKNOWLEDGEMENT OF GOVERNMENT SUPPORT

This invention was made with government support under Grant No. CA067771 awarded by the National Institute of Health. The Government has certain rights in the invention.

BACKGROUND

Rho associated protein kinases (ROCKs) are Ser/Thr protein kinases, activated by small GTPases of the Rho family that act as molecular switches to mediate cell signaling. The Rho/ROCK signaling pathway is known to participate in the regulation of numerous cellular functions such as actin cytoskeleton organization, contraction, cell adhesion, motility, morphology, proliferation, cytokinesis, gene expression, and angiogenesis.

Two isoforms, ROCK1 and ROCK2, have been identified sharing 64% and 79% overall sequence identity and similarity respectively and 92% identity and 97% similarity in their kinase domains. The two isoforms have been found to possess differential tissue distribution. ROCK1 is expressed in lung, liver, stomach, spleen, kidney and testis, whereas ROCK2 is highly expressed in brain, heart and muscle tissues (Nakagawa, et al., *FEBS Lett*, 1996, 392:189-193). Despite the differential tissue distribution, little is known about the functional differences between the two ROCK isoforms (Sapet, et al., *Blood*, 2006, 108:1868-1876; Chang, et al., *Proc Natl Acad Sci USA*, 2006, 103:14495-14500; Sebbagh, et al., *Nat Cell Biol*, 2001, 3:346-352; Thumkeo, et al., *Mol Cell Biol*, 2003, 23:5043-55; Shimizu, et al., *J Cell Biol*, 2005, 168:941-53; Zhang, et al., *Faseb J*, 2006, 20:916-925; Rikitake, et al., *Circulation*, 2005, 112:2959-2965; Coleman, et al., *Nat Cell Biol*, 2001, 3:339-45; Sebbagh, et al., *J Exp Med*, 2005, 201:465-471).

ROCKs have been subjected to growing attention, having been implicated in a range of therapeutic areas including cardiovascular diseases (Shimokawa, et al., *Trends Pharmacol Sci*, 2007, 28:296-302; Xing, et al., *Drug News Perspect*, 2006, 19:517-522; Liao, et al., *J Cardiovasc Pharmacol*, 2007, 50:17-24; Shimokawa, et al., *Arterioscler Thromb Vasc Biol*, 2005, 25:1767-1775; Dong, et al., *Cardiovasc Hematol Agents Med Chem*, 2009, 7:322-330), CNS disorders (Kubo, et al., *Recent Pat CNS Drug Discov*, 2007, 2:173-9; Kubo, et al., *Ther Clin Risk Manage*, 2008, 4:605-615), inflammation (LoGrasso Philip, et al., *Curr Top Med Chem*, 2009, 9:704-23), and cancer (Suwa, et al., *Br J Cancer*, 1998, 77:147-152; Kamai, et al., *Clinical Cancer Research*, 2004, 10:4799-4805; Schmitz, et al., *Exp Cell Res*, 2000, 261:1-12; Imamura, et al., *Jpn J Cancer Res*, 2000, 91:811-816; Somlyo, et al., *Biochem Biophys Res Commun*, 2000, 269:652-659; Uchida, et al., *Biochem Biophys Res Commun*, 2000, 269:633-640; Itoh, et al., *Nat Med (NY)*, 1999, 5:221-225; Uehata, et al., *Nature*, 1997, 389:990-4; Ishizaki, et al., *Mol Pharmacol*, 2000, 57:976-983; Narumiya, et al., *Methods Enzymol*, 2000, 325:273-84; Nakajima, et al., "Cancer Chemother Pharmacol, 2003a, 52:319-24; Nakajima, et al., *Eur J Pharmacol*, 2003b, 459:113-20; Ying, et al., *Mol Cancer Ther*, 2006, 5:2158-2164; Somlyo, et al., *Faseb J*, 2003, 17:223-234; Hampson, et al., *Br J Cancer*, 2009, 101:829-839; Igishi, et al., *Int J Oncol*, 2003, 23:1079-1085; Liu, et al., *Cancer Res*, 2009, 69:8742-8751; Ogata, et al., *Int J Gynecol Cancer*, 2009, 19:1473-80; Zohrabian, et al., *Anticancer Res*, 2009, 29:119-123).

Cooverexpression of Rho and ROCK proteins in cancer cells has been reported in ovarian cancer, pancreatic, testicular, and bladder cancer (Suwa et al. (1998); Kamai et al. (2004)). Metastasis requires changes in the migratory, invasivee and adhesive properties of tumor cells. These processes which depend on the proper assembly/disassembly of actincytoskeleton are regulated by Rho/ROCK pathway and play an important role in the development and progression of cancer (Schmitz et al. (2000)). The implication of Rho/ROCK signalling pathway in invasion by tumor cells (Imamura et al. (2000); Somlyo et al. (2000)), angiogenesis (Uchida et al. (2000)), and their evolution to metastasis (Itoh et al. (1999)) has been amply documented. In light of these findings, the pharmacological inhibition of ROCKs has been suggested as a promising strategy in the prevention of cell invasion, a central event in the process of metastasis (Itoh et al. (1999); Uehata et al. (1997); Ishizaki et al. (2000); Narumiya et al. (2000)).

The potential of ROCK inhibitors as anticancer agents was demonstrated by the identification of ATP competitive inhibitors, Y27632 (1), and Wf536 (2) (FIG. 1) (Itoh et al. (1999); Nakajima et al. (2003a); Nakajima et al. (2003b); Somlyo et al. (2000)). Specifically, 1 was reported to reduce metastasis in animal model systems (Itoh et al. (1999)), and 2 has shown efficacy in preventing tumor metastasis in vivo models by inhibiting tumor-induced angiogenesis as well as tumor motility (Nakajima et al. (2003a); Nakajima et al. (2003b); Somlyo et al. (2003)). Han and coworkers have also investigated the ability of Fasudil (3) (5-(1,4-diazepane-1-sulfonyl)isoquinoline) (the only ROCK inhibitor clinically approved in Japan for the treatment of cerebral vasospasm) to inhibit progression of human and rat tumors in animal models (Ying et al. (2006)).

Significant research efforts have been directed towards the identification of more potent and more selective ROCK inhibitors (Chen, et al., *Bioorg. Med. Chem. Lett.*, 2008, 18:6406-6409; Sessions, et al., *Bioorg. Med. Chem. Lett.*, 2008, 18:6390-6393; Iwakubo, et al., *Bioorg. Med Chem.*, 2007, 15:1022-1033; Goodman, et al., *J. Med Chem.*, 2007, 50:6-9; Feng, et al., *J. Med Chem.*, 2008, 51:6642-6645; Sehon, et al., *J. Med. Chem.*, 2008, 51:6631-6634) including isoquinolinamines (Ray, J et al., *Bioorg. Med. Chem. Lett.*, 2011, 21:97-101; Ray, et al., *Bioorg. Med. Chem. Lett.*, 2011, 21:1084-1088), triazines (Ho, et al., *Bioorg. Med. Chem. Lett.*, 2009, 19:6027-6031), isoquinolinones (Bosanac, et al., *Bioorg. Med Chem. Lett.*, 2010, 20:3746-3749; Ginn, et al., *Bioorg. Med. Chem. Lett.*, 2010, 20:5153-5156), quinazolinones (Fang, et al., *Bioorg. Med. Chem. Lett.*, 2011, 21:1844-1848), benzothiazoles (Yin, et al., *Bioorg. Med Chem. Lett.*, 2009, 19:6686-6690) and diaminopyrazines (Henderson, et al., *Bioorg. Med. Chem. Lett.*, 2010, 20:1137-1140) and their use for the treatment of cardiovascular diseases and CNS disorders. The antitumor and antimetastatic properties of these inhibitors has yet to be shown or published.

The aminothiazole derivative CID5056270 (4)(FIG. 2) has been reported (Feng, et al., *J. Med Chem.*, 2008, 51:6642-6645) to potently inhibit ROCK2 enzymatic activity with an $IC_{50}$ values<3 nM. It displayed high potency in (FRET)-based Z'-Lyte biological assay (Kang, et al., *Bioorg. Med Chem. Lett.*, 2009, 19:533-537; Koresawa, et al., *Assay Drug Dev. Technol.*, 2004, 2:153-160) (ROCK2 $IC_{50}$ 0.56 nM) and also inhibited ROCK1 with an $IC_{50}$ of 13 nM (FIG. 2). In view of its potency against both ROCK isoforms and selectivity over Aurora-A ($IC_{50}$>100 µM) (FIG. 2), 4 has been a starting point for the design of ROCK inhibitors. Specifically, several pyridylthiazole ureas, such as 5a, have been synthesized and tested as ROCK inhibitors (WO 2011/130740). While many of these compounds were highly potent, further inhibitors are still needed. Disclosed herein are compounds and methods that address these and other needs.

SUMMARY

In accordance with the purposes of the disclosed materials, compounds, compositions, articles, devices, and methods, as embodied and broadly described herein, the disclosed subject matter relates to compositions and methods of making and using the compositions. In other aspect, the disclosed subject matter relates to compounds having activity as inhibitors of Rho-associated proteinkinases (ROCKs), methods of making and using the compounds, and compositions comprising the compounds. In certain aspects, the disclosed subject matter relates to compounds having the chemical structure shown in Formula I or Formula II.

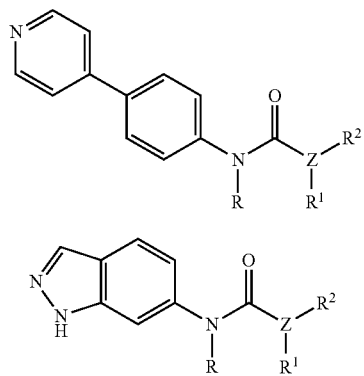

wherein
Z is CR or N;
R is H, alkyl, acetyl, or heteroalkyl;
$R^1$ is H, alkyl, acetyl, or heteroalkyl;
$R^2$ is alkyl, cycloalkyl, heterocycloalkyl, aryl, heteroaryl, or alkylaryl, any of which can be optionally substituted with one or more of —OH, —$CH_2OH$, —C(O)$NH_2$, acetyl, carbonyl, alkyl, cycloalkyl, heterocycloalkyl, aryl, or heteroaryl, any of which can be optionally substituted with one or more of —OH, —$NO_2$, —$NH_2$, —$NR^6R^7$, alkyl, alkoxy, alkylalkoxy, alkoxylalkoxy, halogenated alkoxy, heteroarylcarbonyl, heteroaryl, —$OCX_3$, —$OCHX_2$, —$OCH_2X$, —$OSO_2CH_3$, tosyl, or halogen; or $R^1$ and $R^2$ can together form a cycloalkyl or heterocycloalkyl
$R^6$ and $R^7$ are, independently, H, alkyl, —$SO_2CH_3$, —C(O)$CH_3$, or —C(O)$NH_2$;
X is independently H or halogen;
or a pharmaceutically acceptable salt or hydrate thereof.

In still further aspects, the disclosed subject matter relates to methods for treating oncological disorders in a patient. For example, disclosed herein are methods whereby an effective amount of a compound or composition disclosed herein is administered to a patient having an oncological disorder and who is in need of treatment thereof. Similarly, the disclosed subject matter relates to methods of treating cardiovascular disorders.

Additional advantages of the disclosed subject matter will be set forth in part in the description that follows and the Figures, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF FIGURES

The accompanying figures, which are incorporated in and constitute a part of this specification, illustrate several aspects described below.

FIG. 2 shows the structure of CDI5056270 (4) and compound 5a.

FIG. 3A: Surface presentation of the ROCK1 dimer in complex with 18 determined by X-ray crystallography at 2.3 Å resolution. Exploded view detailing the binding interactions of 18 within the ATP site; the hinge and DFG regions are indicated in cyan and orange, respectively. Displayed in blue is the $2F_o$-$F_c$ electron density, contoured at 1 σ around the inhibitor. Potential hydrogen bonding and van der Waal interactions are shown as black and green dotted lines, respectively. FIG. 3B: Schematic presentation of the binding interactions between 18 and the ATP site. FIG. 3C: Overlay of compound 18 in the active site of Rock1 determined by X-ray crystallography (yellow) and predicted by molecular modeling (green).

FIG. 7C: Cells were treated with either vehicle or various concentrations of RKIs (0.05-50 mM) for 72 h and stained with MTT (2 mg/ml). Data are representative of two independent experiments.

FIG. 8A: Cells were plated at 4×10$^5$ cells per well, starved for 24 h, scratched and treated with vehicle or RKIs as described under Materials and methods section (data representative of three independent experiments). FIG. 8B: MDA-MB-231 cells were treated with vehicle or RKIs, and plated at 20 000 cells per insert in Corning Transwell inserts coated with Matrigel, and allowed to invade for 48 h, after which they were analyzed as described under Materials and methods. Data shows average of three independent experiments.

DETAILED DESCRIPTION

Figure 1:
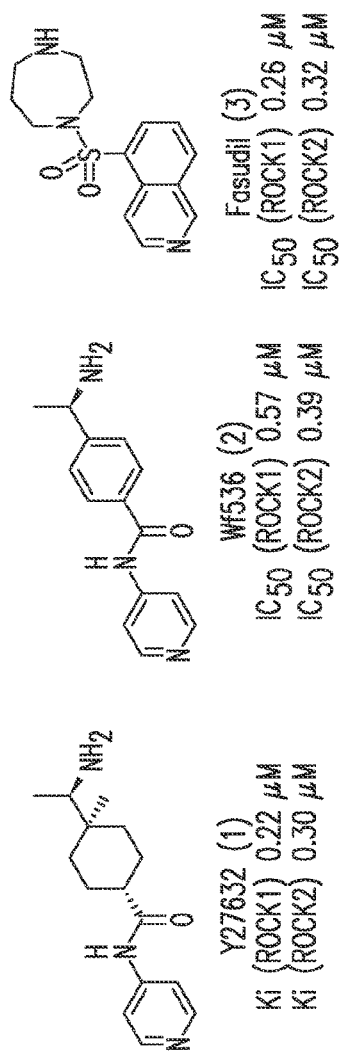
FIG. 1 shows known Rho kinase inhibitors.
Figure 2:
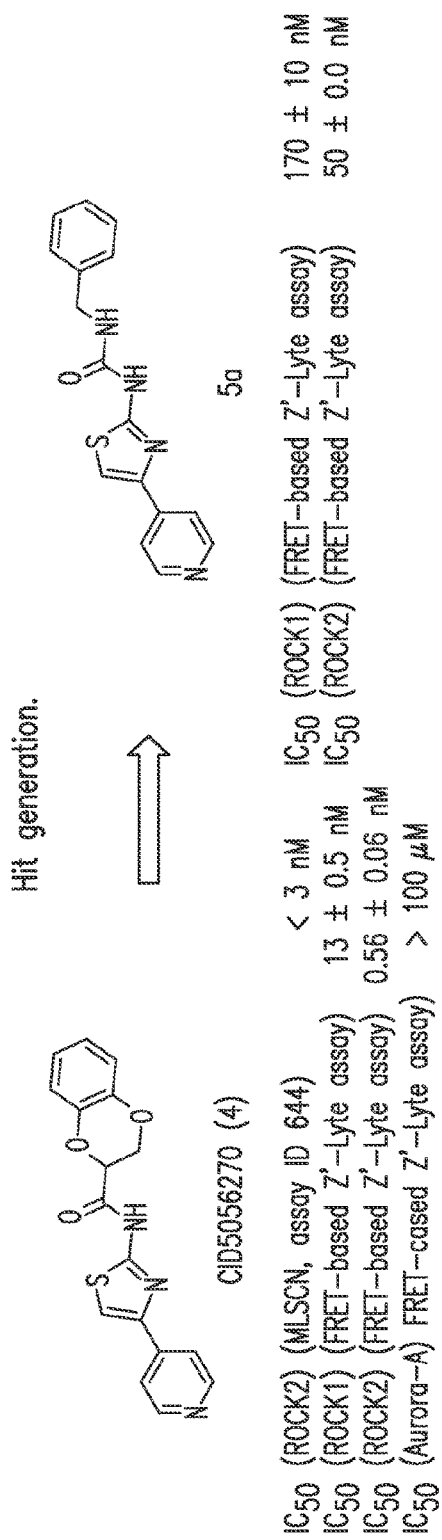

The compounds, compositions, articles, devices, and methods described herein may be understood more readily by reference to the following detailed description of specific aspects of the disclosed subject matter and the Examples included therein and to the Figures.

Before the present compounds, compositions, articles, devices, and methods are disclosed and described it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$— where $Z^1$ is alkyl as defined above.

The term "alkenyl" as used herein is a hydrocarbon group of from 2 to 24 carbon atoms with a structural formula containing at least one carbon-carbon double bond. Asymmetric structures such as ($Z^1Z^2$)C=C($Z^3Z^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus.

The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O.

The terms "amine" or "amino" as used herein are represented by the formula —$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)$Z^1$ or —C(O)O$Z^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —Si$Z^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

The examples below are intended to further illustrate certain aspects of the methods and compounds described herein, and are not intended to limit the scope of the claims.

Reference will now be made in detail to specific aspects of the disclosed compounds, compositions, articles, devices, and methods, examples of which are illustrated in the accompanying Examples and Figures.

Compounds

Disclosed are compounds that have activity as inhibitors of Rho-associated proteinkinases (ROCKs), methods of making and using the compounds, and compositions comprising the compounds. In certain embodiments, the disclosed compounds have the chemical structure shown in Formula I or Formula II.

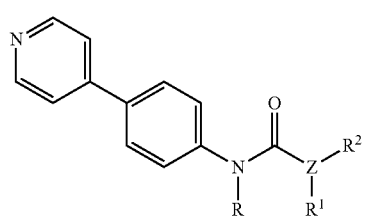

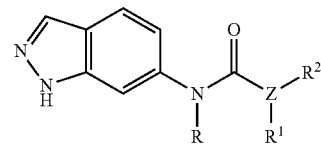

wherein

Z is CR or N;

R is H, alkyl, acetyl, or heteroalkyl;

$R^1$ is H, alkyl, acetyl, or heteroalkyl;

$R^2$ is alkyl, cycloalkyl, heterocycloalkyl, aryl, heteroaryl, or alkylaryl, any of which can be optionally substituted with one or more of —OH, —$CH_2OH$, —C(O)$NH_2$, acetyl, carbonyl, alkyl, cycloalkyl, heterocycloalkyl, aryl, or heteroaryl, any of which can be optionally substituted with one or more of —OH, —$NO_2$, —$NH_2$, —$NR^6R^7$, alkyl, alkoxy, alkylalkoxy, alkoxylalkoxy, halogenated alkoxy, heteroarylcarbonyl, heteroaryl, —$OCX_3$, —$OCHX_2$, —$OCH_2X$, —$OSO_2CH_3$, tosyl, or halogen; or $R^1$ and $R^2$ can together form a cycloalkyl or heterocycloalkyl $R^6$ and $R^7$ are, independently, H, alkyl, —SO$_2$CH$_3$, —C(O)CH$_3$, or —C(O)NH$_2$;

X is independently H or halogen;

or a pharmaceutically acceptable salt or hydrate thereof.

In one embodiment, $R^2$ is alkyl. In a specific embodiment, $R^2$ is alkyl substituted with at least an aryl. In a more specific embodiment, $R^2$ is alkyl (such as methyl) substituted with a phenyl (resulting in an alkylaryl group). In a still further embodiment, $R^2$ is alkyl (such as methyl or ethyl) substituted with a phenyl which is substituted with an alkoxy group (such as methoxy or ethoxy).

In some embodiments, when the compound of Formula II (or IV) has R and $R^1$ both H, $R^2$ is not CH$_2$Ph, CH(CH$_2$OH)Ph, CH$_2$CH$_2$Ph, or CH(CH$_2$OH)CH$_2$Ph.

In a more specific aspect, disclose herein are compounds having a chemical structure shown in Formula III or Formula IV.

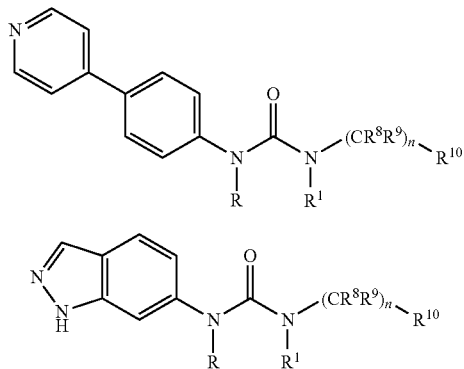

III

IV wherein n is 1, 2, or 3;

R and $R^1$ are, independently, H, alkyl, acetyl, or heteroalkyl;

$R^8$ and $R^9$ are, independently of one another, H, —OH, acetyl, —C(O)NH$_2$, alkyl, cycloalkyl, hereterocycloalkyl, aryl, or heteroaryl, wherein any one of the alkyl, cycloalkyl, hereterocycloalkyl, aryl, or heteroaryl groups is optionally substituted with one or more of —OH, —NO$_2$, —NH$_2$, —NR$^6$R$^7$, carbonyl, alkoxy, alkyl, —OCX$_3$, —OCHX$_2$, —OCH$_2$X, or halogen, or both $R^8$ together form a carbonyl;

$R^{10}$ is cycloalkyl, heterocycloalkyl, aryl, or heteroaryl, any of which is optionally substituted with one or more of —OH, —C(O)NH$_2$, —C(O)CH$_3$, —NO$_2$, —NH$_2$, —NR$^6$R$^7$, carbonyl, alkyl, alkoxy, alkylalkoxy, alkoxylalkoxy, halogenated alkoxyl, cycloalkyl, heterocycloalkyl, heteroarylcarbonyl, aryl, heteroaryl, —OCX$_3$, —OCHX$_2$, —OCH$_2$X, —OSO$_2$CH$_3$, -tosyl, or halogen;

$R^6$ and $R^7$ are, independently, H, alkyl, —SO$_2$CH$_3$, —C(O)CH$_3$, or —C(O)NH$_2$; and X is independently H or halogen;

or a pharmaceutically acceptable salt or hydrate thereof.

In specific examples, n is 1. In other examples, n is 2. $R^8$ and $R^9$ can be, independently of one another, H, alkyl, or alkyl substituted with —OH, —NH$_2$, alkoxy, or halogen. In some examples, n is 1, and CR$^8$R$^9$ can be the R isomer of CHalkyl or the S isomer of CHalkyl, wherein the alkyl group is substituted with —OH, NH$_2$, alkoxy, or halogen. $R^{10}$ can preferably be aryl or heteroaryl substituted in the ortho, meta, or para position. For example, $R^{10}$ can be an aryl or heteroaryl, optionally substituted in the ortho-, meta-, or para-position with —OH, —C(O)NH$_2$, —NO$_2$, —NH$_2$, —NR$^6$R$^7$, alkoxy, alkylalkoxy, alkyl, or halogen. In other examples, n is 2 and each $R^8$ and $R^9$ are H, and $R^{10}$ is phenyl.

In still other embodiments, the disclosed compounds have the chemical structure shown in Formula V or Formula VI.

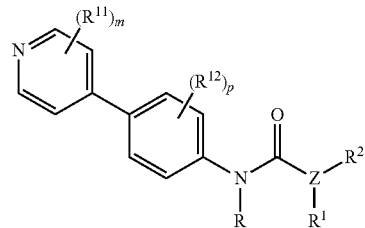

V

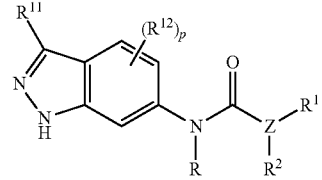

VI wherein

Z, R, $R^1$, $R^2$, $R^6$, $R^7$, and X are as defined herein;

m is 1, 2, 3, or 4, indicating that there can be 1, 2, 3, or 4 $R^{11}$ substituents on the pyridiyl ring;

each $R^{11}$ is, independently of one another, H, —C(O)NH$_2$, —C(O)CH$_3$, —CO$_2$H, —CO$_2$alkyl, —NO$_2$, —NH$_2$, —NR$^6$R$^7$, carbonyl, alkyl, alkoxy, alkylalkoxy, alkoxylalkoxy, halogenated alkoxyl, cycloalkyl, heterocycloalkyl, heteroarylcarbonyl, aryl, heteroaryl, —OCX$_3$, —OCHX$_2$, —OCH$_2$X, —OSO$_2$CH$_3$, -tosyl, or halogen;

p is 1, 2, 3, or 4 in Formula V, indicating that there can be 1, 2, 3, or 4 $R^{12}$ substituents on the phenyl ring; or p is 1, 2, or 3 in Formula VI, indicating that there can be 1, 2, or 3 $R^{12}$ substituents on the indazole ring; and each $R^{12}$ is, independently of one another, H, —C(O)NH$_2$, —C(O)CH$_3$, —CO$_2$H, —CO$_2$alkyl, —NO$_2$, —NH$_2$, —NR$^6$R$^7$, carbonyl, alkyl, alkoxy, alkylalkoxy, alkoxylalkoxy, halogenated alkoxyl, cycloalkyl, heterocycloalkyl, heteroarylcarbonyl, aryl, heteroaryl, —OCX$_3$, —OCHX$_2$, —OCH$_2$X, —OSO$_2$CH$_3$, -tosyl, or halogen;

or a pharmaceutically acceptable salt or hydrate thereof.

In still other embodiments, the disclosed compounds have the chemical structure shown in Formula VII or Formula VIII.

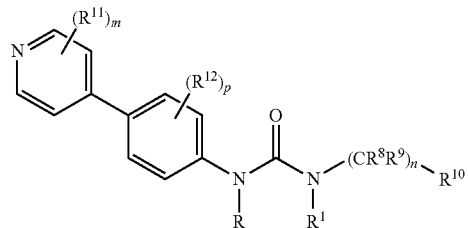

VII

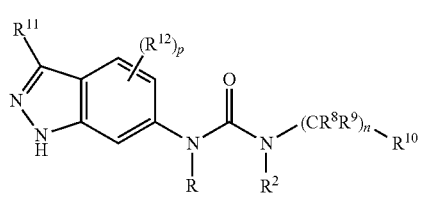

wherein
R, $R^1$, $R^2$, $R^6$, $R^7$, $R^8$, $R^9$, $R^{10}$, $R^{11}$, $R^{12}$, X, n, m, and p are as defined herein.

The structures in Formulas V and VII are similar to those of Formulas I and III, and the structures in Formula VI and VIII are similar to those of Formulas II and IV, respectively, except for the presence of substituents on the pyridine, phenyl, and/or indazole rings. A binding analysis indicates that there is space in the binding pocket to accommodate substituents on the pyridine, phenyl, and/or indazole ring. Thus, disclosed herein are compounds of Formulas V and VII where m can be 1 and $R^{11}$ is at the 2 position or the 3 position of the pyridyl ring. In other embodiments, m can be 2 and the two $R^{11}$ substituents are at the 2 and 3 positions, the 2 and 5 positions, or the 2 and 6 positions of the pyridyl ring. Still further, m can be 3 and the three $R^{11}$ substituents can be at the 2, 3, and 5 positions, the 2, 3, and 6 positions of the pyridyl ring. Also, m can be 4 and thus four $R^{11}$ substituents are present at the 2, 3, 5, and 6 positions of the pyridyl ring. Any of these examples can likewise have 1, 2, 3 or 4 $R^{12}$ substituents, which are defined herein, on the phenyl ring. In a preferred example, $R^{11}$ is an electron donating substituent.

In Formulas VI and VIII there can be an $R^{12}$ substituent at the 2, 4, or 5 position of the indazole ring, two $R^{12}$ substituents at the 2 and 4, 2 and 5, or 4 and 5 positions at the indazole ring, or three $R^{12}$ substituents at the 2, 4, and 5 position. Any of these examples can likewise have a $R^{11}$ substituent as defined herein.

In certain examples, m is 1 and $R^{11}$ is at the 2 position and is F, Cl, Me, or $NH_2$. In other examples, $R^{12}$ is alkyl or $CO_2$alkyl.

Making reference to Formulas III and IV as well as VII and VII, some specific examples of compounds disclosed herein haven as 1, $R^8$ and $R^9$ as both H, and $R^{10}$ having a structure selected from the following. With reference to Formulas I and II as well as V and VI, additional compounds disclosed herein have $R^2$ being selected from the following structures.

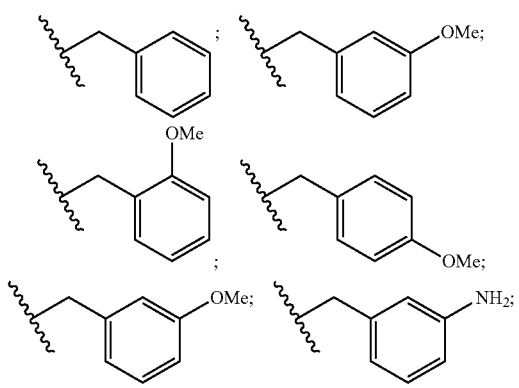

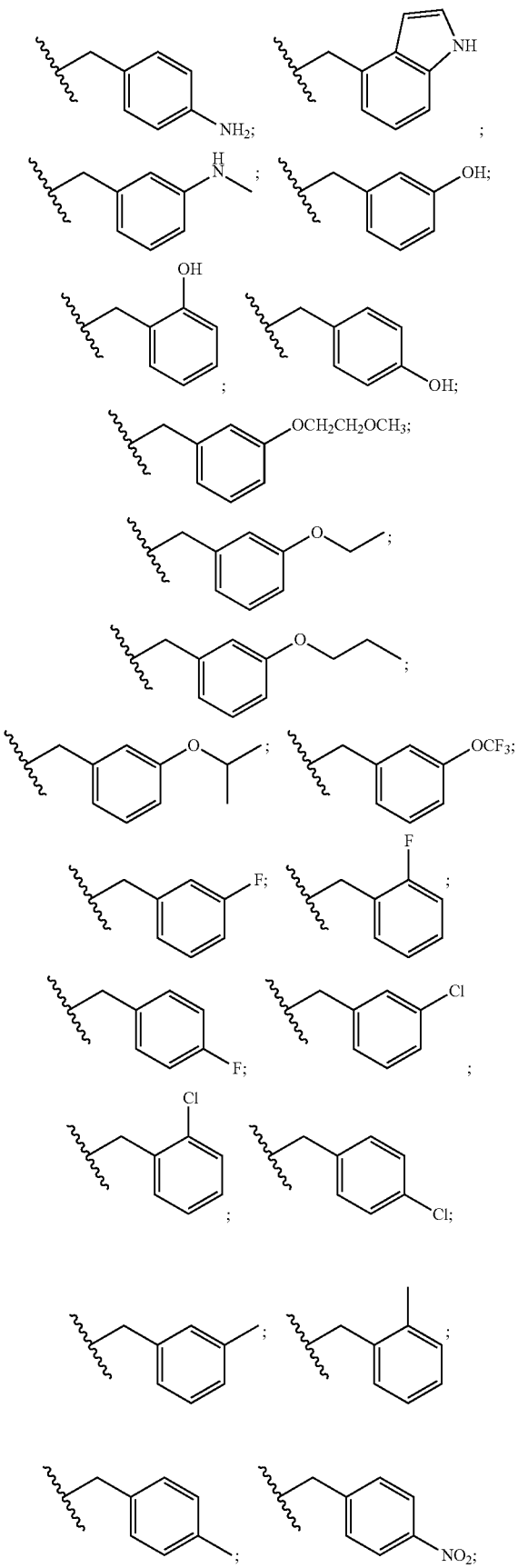

-continued

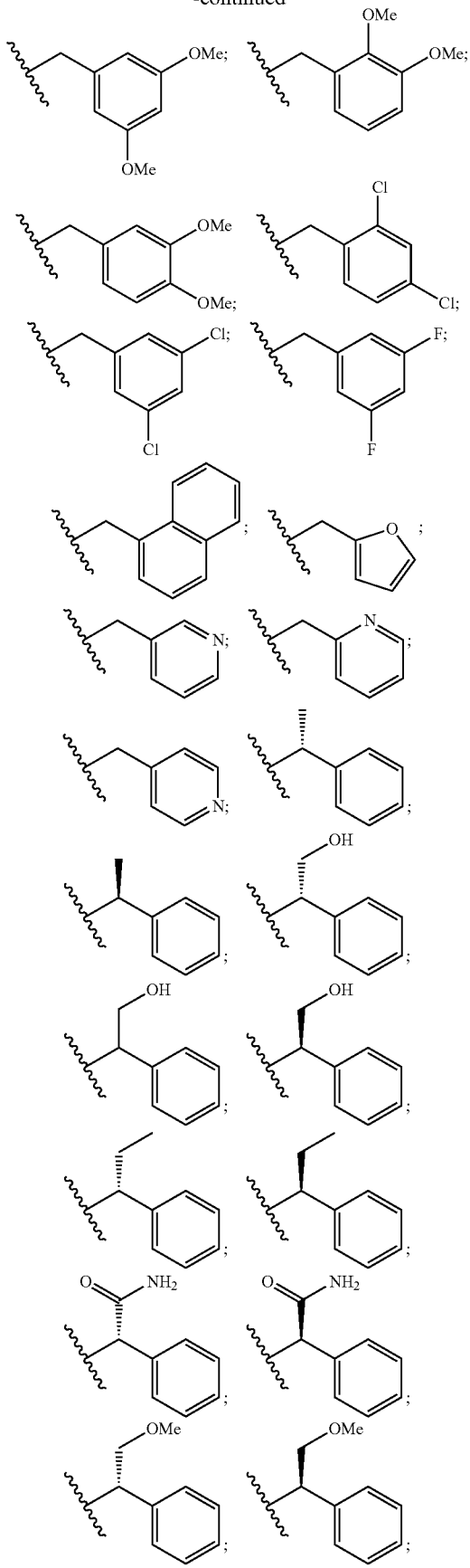

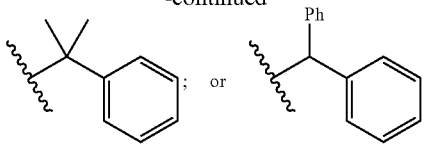

wherein | indicates the point of attachment to Z in Formulas I, II, V, and VI or N(R¹) in Formulas III, IV, VII, and VIII. Me is methyl, and Ph is phenyl.

In other examples, when in any formula $R^2$ is benzyl (or $CR^8R^9$ is $CH_2$, n=1, and $R^{10}$ is phenyl), the aryl group can be substituted with a mesyl —$OSO_2CH_3$, or tosyl, brosyl, triflate, or other electron withdrawing group.

Also disclosed herein are pharmaceutically-acceptable salts and hydrates of the disclosed compounds. Pharmaceutically-acceptable salts include salts of the disclosed compounds that are prepared with acids or bases, depending on the particular substituents found on the compounds. Under conditions where the compounds disclosed herein are sufficiently basic or acidic to form stable nontoxic acid or base salts, administration of the compounds as salts can be appropriate. Examples of pharmaceutically-acceptable base addition salts include sodium, potassium, calcium, ammonium, or magnesium salt. Examples of physiologically-acceptable acid addition salts include hydrochloric, hydrobromic, nitric, phosphoric, carbonic, sulphuric, and organic acids like acetic, propionic, benzoic, succinic, fumaric, mandelic, oxalic, citric, tartaric, malonic, ascorbic, alpha-ketoglutaric, alpha-glycophosphoric, maleic, tosyl acid, methanesulfonic, and the like. Thus, disclosed herein are the hydrochloride, nitrate, phosphate, carbonate, bicarbonate, sulfate, acetate, propionate, benzoate, succinate, fumarate, mandelate, oxalate, citrate, tartarate, malonate, ascorbate, alpha-ketoglutarate, alpha-glycophosphate, maleate, tosylate, and mesylate salts. Pharmaceutically acceptable salts of a compound can be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds containing a pyridyl group as a "hinge" binder to Rho kinases are disclosed in Table 1. Their molecular weights range from 199 to 293 Dalton. Coupling of para-aminopyridine with nicotinic acid, picolinic acid, isonicotinic acid, 4-chloronicotinic acid and 5-bromonicotinc acid using EDC in DMF yielded the corresponding amides (1-5). A para-fluorophenyl group was installed within compound 4 and 5 via a Suzuki reaction to give rise to 6 and 7, respectively. This library was subjected to high concentration (400 μM) biochemical assays to determine their in vitro inhibitory activities against ROCK 1 and ROCK 2 kinases. While both picolinamide (1) and isonicotinamide (2) showed only 30-40% inhibition on both ROCK 1 and ROCK 2 at 400 μM, nicotinamide (3) had $IC_{50}$ values of 75.5 μM and 55.9 μM for ROCK 1 and ROCK 2, with Ligand Efficiencies (LE≈_G/HAC, defined as the free energy of binding divided by the number of non-hydrogen/heavy atoms) of 0.37 and 0.39, respectively. 4-Chlorosubsituted nicotinamide (4) decreased the inhibitory activity against ROCK 2 by 4 fold. 5-Bromosubstituted nicotinamide (5) decreased ROCK 1 and ROCK 2 inhibitory activities by up to six fold. Larger substituent (para-fluorophenyl) at the corresponding positions (6 and 7) diminished the activity even further (Table 1). These results indicate that the fragments (4-7) bearing bulkier functional group in the 4 or 5-position of nicotinamide can interfere with their binding to the hinge region due to steric clashes.

TABLE 1

Synthesis of Fragments 1-7, IC$_{50}$ and LE Values

| Compd | MW | ROCK1 (IC$_{50}$, µM)$^a$ | LE$^c$ | ROCK2 (IC$_{50}$, µM)$^a$ | LE$^c$ |
|---|---|---|---|---|---|
| 1 | 199.21 | 35% inhibition$^b$ | | 35% inhibition$^b$ | |
| 2 | 199.21 | 44% inhibition$^b$ | | 42% inhibition$^b$ | |
| 3 | 199.21 | 75.5 ± 18.9 | 0.37 | 55.9 ± 11.3 | 0.39 |
| 4 | 233.65 | 72.5 ± 6.8 | 0.35 | 221.4 ± 25.7 | 0.31 |
| 5 | 278.10 | 270.0 ± 51.0 | 0.30 | 357.2 ± 35.3 | 0.29 |
| 6 | 293.30 | >400 | <0.2 | >400 | <0.2 |
| 7 | 293.30 | >400 | <0.2 | >400 | <0.2 |

$^a$Data from triplicate experiments.
$^b$Compound concentration at 400 µM.
$^c$Ligand Efficiency.
1: R = H, picolinamide
2: R = H, isonicotinamide
3: R = H, nicotinamide
4: R = 4-Cl, nicotinamide
5: R = 5-Br, nicotinamide
6: R = 4-(para-fluorophenyl), nicotinamide
7: R = 5-(para-fluorophenyl), nicotinamide 5-Aminoindazole (8) was chosen as a substitute fragment for para-aminopyridine. The distances from the amino nitrogen to 1-indazole nitrogen and 2-indazole nitrogen are 5.5 and 5.9 Å, respectively, whereas the distance from the para-amino nitrogen to pyridine nitrogen is only 4.2 Å. Fragment 8 showed IC$_{50}$ values of 181 µM for ROCK 1 and 120 µM against ROCK 2 with LE being 0.51 and 0.53, respectively (Table 2). Although N-(1H-indazole-5-yl)acetamide demonstrated improved potency (65 µM for ROCK 1 and 40 µM for ROCK 2), the amides derived from the corresponding aromatic carboxylic acids did not yield potency-improved compounds.

As shown in Table 2, dimethyl/indazole urea 10 had improved potency with IC$_{50}$ values of 59 µM for ROCK 1 and 36 µM against ROCK 2 with LEs being 0.38 and 0.40, respectively. However, substitution of one of the methyl groups by a phenyl group and the other with a hydrogen (compound 11) diminished activity. Addition of a methylene moiety between the urea nitrogen and phenyl group of 11 resulted in compound 12 (IC$_{50}$=14 µM and 5.5 µM for ROCK 1 and ROCK 2, respectively) with over an 11-fold improvement in potency. Compound 12 was reported as a ROCK 2 inhibitor with an IC$_{50}$ value of 260 nM along with three other analogs of chloro- or fluoro substituted phenyl groups. Iwakubo, et al., *Bioorg Med Chem* 2007, 15:350-364; Takami, et al., *Bioorg Med Chem* 2004, 12:2115-2137). There was 20-50 fold difference in IC$_{50}$ values between compound 12 and that previously reported, which is likely due to different assay conditions.

Compounds with a two carbon spacer between the urea nitrogen and the phenyl group are also disclosed (e.g., 13-18). Compound 18 showed an IC$_{50}$ of 650 nM and 670 nM for ROCK 1 and ROCK 2, respectively with a 21- and 242-fold improvement in potency (ROCK 1) over compounds 12 and 11, respectively, (Table 2) indicating that the ethylene linker distance allowed the phenyl group to reach a deep hydrophobic pocket within the enzyme binding site of ROCK. However, compound 19 with a three carbon spacer decreased the inhibitory activities by 3.8 fold for ROCK 1 and 1.6 fold for ROCK 2, respectively (IC$_{50}$=2.46 µM and 1.07 µM for ROCK 1 and ROCK 2) with decreased LEs, suggesting the ethylene linker in 18 is the optimal spacer in this series. Addition of methylenehydroxyl group to the ethylene as in 14 and hydroxyl group to the ethylene in 15 or addition of a methoxy or a chloro to the phenyl ring as in 16 and 17 all diminished the potency of 18 to varying degrees, further confirming the hydrophobicity of the binding pocket. Replacement of the urea hydrogen atom of 18 with a methyl group gave rise to the much less potent compound 13, possibly due to the lack of essential free hydrogen on one of the urea nitrogen atoms.

Compounds 10-19 were synthesized from commercially available 8 via a common intermediate 9, by reacting 8 with phenylchloroformate in DCM to form an activated carbamate followed by displacement by the corresponding amines.

TABLE 2

Synthesis of Fragments and Compounds 8-19, IC$_{50}$ and LE Values

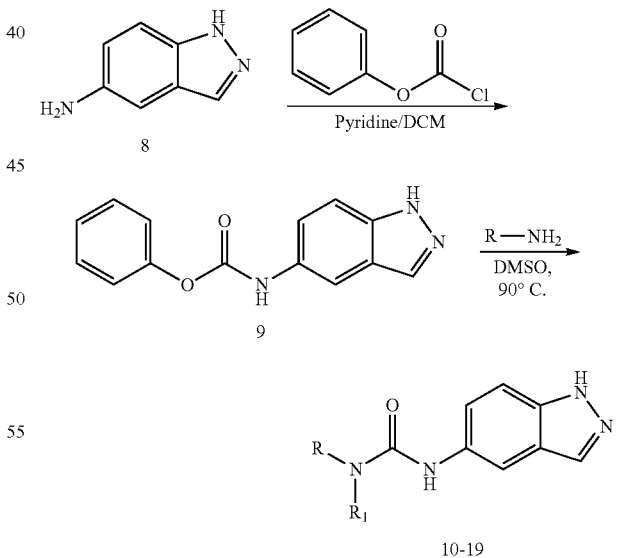

| Compd | MW | ROCK1 (IC$_{50}$, µM)$^a$ | LE$^b$ | ROCK2 (IC$_{50}$, µM)$^a$ | LE$^b$ |
|---|---|---|---|---|---|
| 8 | 133.06 | 181.3 ± 50.7 | 0.51 | 119.7 ± 20.3 | 0.53 |
| 9 | 253.26 | ND$^c$ | | ND$^c$ | |
| 10 | 204.10 | 59.1 ± 15.2 | 0.38 | 36.1 ± 5.9 | 0.40 |
| 11 | 252.10 | 157.1 ± 34.1 | 0.27 | 61.8 ± 9.6 | 0.30 |

TABLE 2-continued

| 12 | 266.12 | 13.9 ± 8.7 | 0.33 | 5.5 ± 3.1 | 0.36 |
| 13 | 294.15 | 21.5 ± 7.3 | 0.27 | 7.5 ± 1.7 | 0.32 |
| 14 | 310.14 | 4.6 ± 2.1 | 0.31 | 2.3 ± 0.6 | 0.33 |
| 15 | 296.13 | 2.9 ± 0.8 | 0.34 | 1.5 ± 0.4 | 0.36 |
| 16 | 310.14 | 2.6 ± 0.6 | 0.33 | 0.8 ± 0.3 | 0.36 |
| 17 | 314.09 | 2.2 ± 1.0 | 0.35 | 1.1 ± 0.3 | 0.37 |
| 18 | 280.13 | 0.65 ± 0.03 | 0.40 | 0.67 ± 0.12 | 0.40 |
| 19 | 294.15 | 2.46 ± 0.55 | 0.35 | 1.07 ± 0.14 | 0.37 |

[a]Data from triplicate experiments.
[b]Ligand Efficiency.
[c]Not determined
10: R = R$_1$ = Me
11: R$_1$ = H, R = Ph
12: R$_1$ = H, R = Bn
13: R$_1$ = Me, R = PhCH$_2$CH$_2$

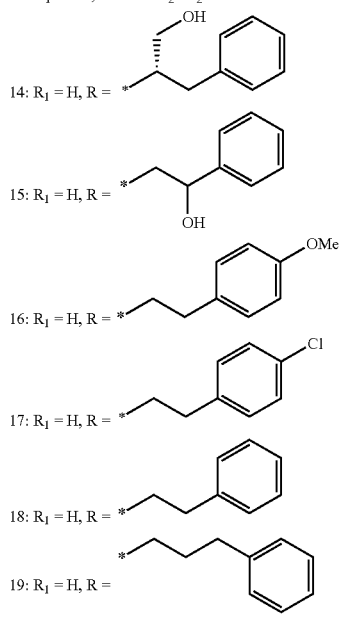

14: R$_1$ = H, R = *
15: R$_1$ = H, R = *
16: R$_1$ = H, R = *
17: R$_1$ = H, R = *
18: R$_1$ = H, R = *
19: R$_1$ = H, R =

A molecular modeling study of a docked structure 18 into ROCK1 (PDB code: 2ESM) (Jacobs, et al., J Biol Chem 2006, 281:260-268) shows that potential hydrogen bonding interactions can be formed between amino acid residues in the hinge region and 18. Potential hydrogen bonding interactions are postulated between the indazole nitrogen and the amide NH from M156, the indazole NH and the carbonyl O from E154 (this binding mode is consistent with that of a co-crystal complex of a reported indazole-containing ROCK1 inhibitor (Sehon, et al., J Med Chem 2008, 51:6631-6634)) and one of the urea NH and carboxylic O from D216 of the DGF motif. However, R84 which is in close proximity was not utilized.

To confirm the possibility of this additional hydrogen bonding, a new fragment 4-(pyridine-4-yl) aniline 20 as a surrogate of indazole 8 was prepared. The distance between the pyridyl nitrogen of 20 and the aniline nitrogen connecting to the urea linker is longer (8.5 Å) than that of 8 (5.9 Å). This shift can allow potential hydrogen bonding interactions with R84.

Six more compounds (22-27) with different spacers were synthesized via the same route as that for synthesis of 10-19 described above and their kinase inhibitory activities were evaluated. The anti-inflammatory activities as ROCK inhibitors of compounds in this series has been confirmed (Yoshimi, et al., J Pharmacol Exp Ther, 2010, 334:955-963). As shown in Table 3, compound 22 with a new hinge binder moiety, 4-(pyridine-4-yl)aniline, showed similar activity to that of 18 (Table 2). Compound 18 has a shorter hinge binder (aminoindazole) but a longer spacer (ethylene) while compound 22 has a longer hinge binder (pyridylaniline) but a shorter spacer (methylene). Their in vitro activities against ROCK 1 and ROCK 2 are from submicromolar to a micromolar (ROCK 1: 0.65 µM for 18 and 1.15 µM for 22; ROCK 2: 0.67 µM for 18 and 0.26 µM for 22, see Table 2 and 3).

Figure 3A:
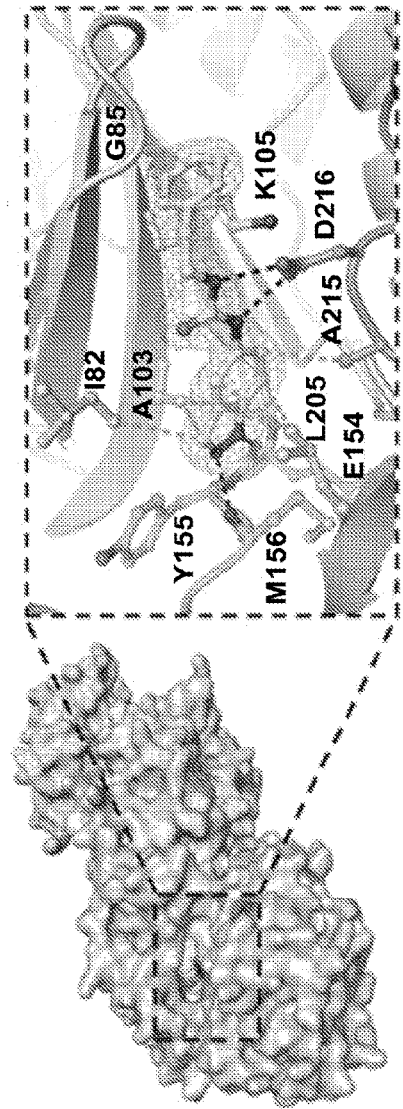
FIGS. 3A-3C show the molecular mode of action of compound 18.
Figure 3C:
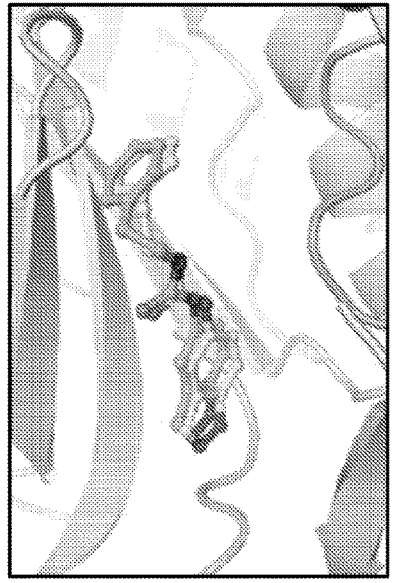
Figure 3B:
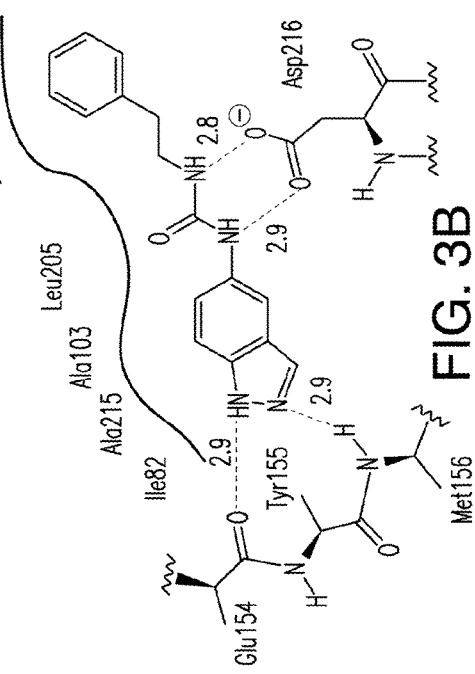
Figure 5:
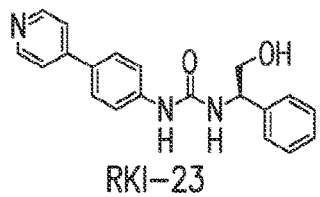
FIG. 5 shows the chemical structures and ROCK inhibition activity of compounds 23 and 24 and compounds 11 and 18.
Figure 5:
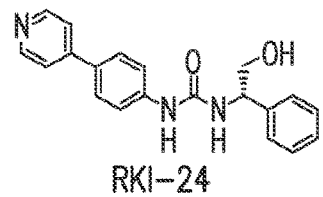
Figure 5:
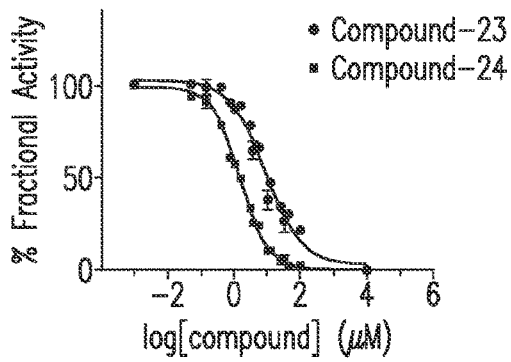
Figure 5:
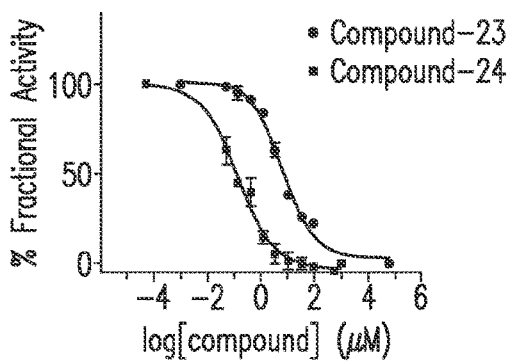
Figure 5:
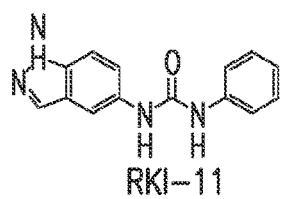
Figure 5:
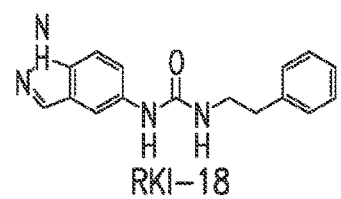
Figure 5:
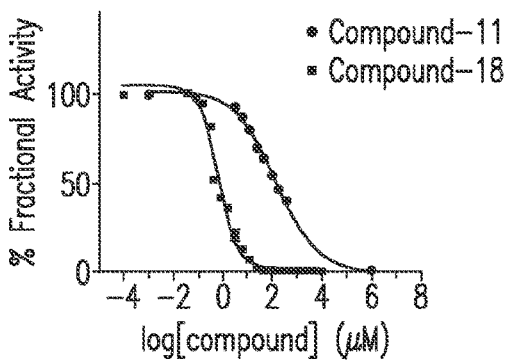
Figure 5:
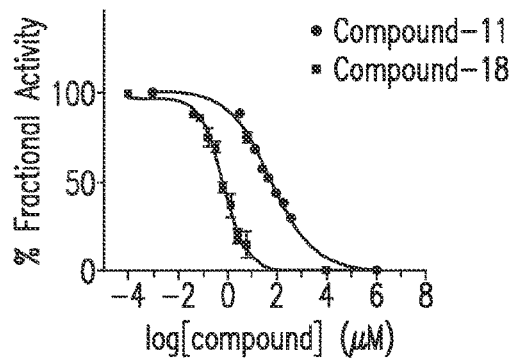

Compound 22 was docked in the same ATP binding pocket as that of 18. While the hydrogen bonding interaction with M156 is retained for 22, the interactions with E154 and D216 are lost. New hydrogen bonding interactions can be achieved between the urea (NH and O) of 22 and R84. Most recently, compound 18 was co-crystallized with the kinase domain of human ROCK1 (residues 6-415) to experimentally determine the mode of action of the indazole containing ROCK1 inhibitor series. The ROCK1 compound 18 complex crystallized in space group C2221 with two dimers per asymmetric unit. The structure was refined to 2.3 Å resolution with R$_{cryst}$ and R$_{free}$ values of 18.8% and 23.6%, respectively. The inhibitor binds to the ATP site of ROCK1 essentially as predicted by molecular docking (FIG. 3C). The indazole nitrogen atoms establish hydrogen bonding interactions with the main chain of residues Met156 and Glu154 of the hinge region. In addition, the indazole ring establishes a series of van der Waals (hydrophobic) interactions with Ile82, Ala215, Ala103 and Leu205 (FIG. 3B). The urea linker interacts with the side chain of Asp216 of the DFG motif. The phenyl ring is sandwiched between the P-loop (Arg84-Gly88) of the upper N-terminal lobe and the side chain of the catalytic residue Lys105 (FIG. 3A). The crystal structure corroborates the results from the molecular modeling studies, and only small changes are observed in the conformation of the inhibitor molecule. Two pairs of chiral spacers were used to probe stereochemical preferences that can exist in the enzyme binding site. Compound 24 with an S-configuration (IC$_{50}$ 100 nM) showed 75 fold more kinase inhibitory activity than compound 23 with a R-configuration (IC$_{50}$ 7520 nM) for ROCK 2 while the difference is only five fold for ROCK1 (IC$_{50}$ 9.07 µM for 23 vs. 1.69 µM for 24) (FIG. 5). However, their corresponding homologs with an additional methylene spacer exhibited the opposite selectivity. While compound 26 with a R-configuration is only six fold more active than that of 27 with an S-configuration towards ROCK 2 (IC$_{50}$ 5.36 µM for 26 vs. 32.92 µM for 27), 22 fold more inhibitory activity towards ROCK 1 is observed (IC$_{50}$ 1.41 µM for 26 vs. 31.01 µM for 27). In addition, compound 26 demonstrated four-fold selectivity for ROCK 1 over ROCK 2. Eight-fold selectivity of ROCK 1 over ROCK 2 is also observed for compound 25 with ethylene spacer (Table 3).

TABLE 3

Synthesis of Compounds 20-27, IC$_{50}$ and LE Values

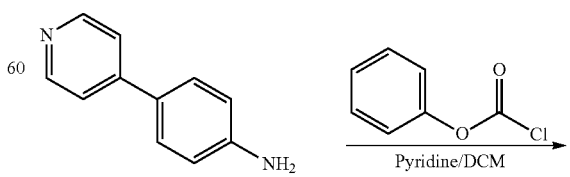

20

TABLE 3-continued

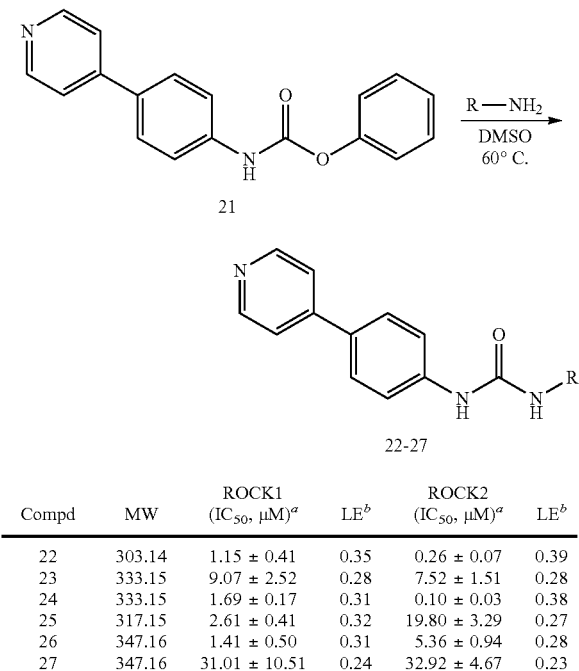

| Compd | MW | ROCK1 (IC$_{50}$, μM)$^a$ | LE$^b$ | ROCK2 (IC$_{50}$, μM)$^a$ | LE$^b$ |
|---|---|---|---|---|---|
| 22 | 303.14 | 1.15 ± 0.41 | 0.35 | 0.26 ± 0.07 | 0.39 |
| 23 | 333.15 | 9.07 ± 2.52 | 0.28 | 7.52 ± 1.51 | 0.28 |
| 24 | 333.15 | 1.69 ± 0.17 | 0.31 | 0.10 ± 0.03 | 0.38 |
| 25 | 317.15 | 2.61 ± 0.41 | 0.32 | 19.80 ± 3.29 | 0.27 |
| 26 | 347.16 | 1.41 ± 0.50 | 0.31 | 5.36 ± 0.94 | 0.28 |
| 27 | 347.16 | 31.01 ± 10.51 | 0.24 | 32.92 ± 4.67 | 0.23 |

$^a$Data from triplicate experiments.
$^b$Ligand Efficiency.

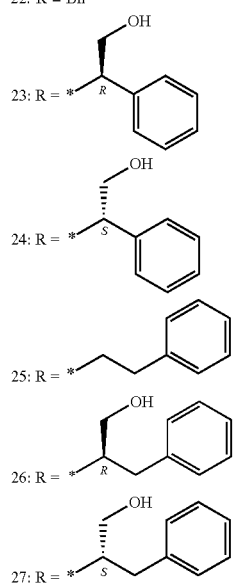

Figure 4:
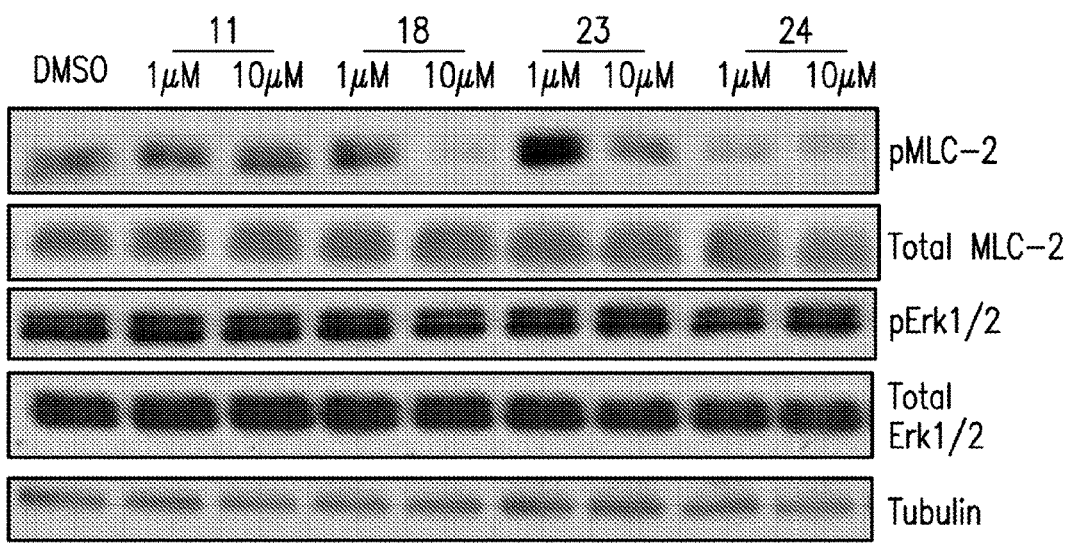
FIG. 4 is an image from a gel electrophoresis showing that Rock inhibitors suppress the phosphorylation of MLC2 in breast cancer cells.

The in vitro kinase SAR yielded potent and selective Rho kinase inhibitors. It was also determined whether these were capable of entering intact cells, reaching their target and inhibiting Rho kinase from phosphorylating its substrate MLC2. To this end, human breast cancer MDA-MB-231 cells were treated for 1 hr with two pairs of compounds 23/24 and 11/18 representing the two classes of inhibitors, and the cells were processed for determining the levels of phosphorylation of MLC2 (PMLC2). FIG. 4 shows that treatment of the breast cancer cells with 24 at 1 μM and 10 μM greatly decreased P-MLC2 levels whereas its stereoisomer 23 had no effect at 1 μM and was less potent than 24 at 10 μM. This is consistent with the in vitro kinase studies where 24 was more potent (IC$_{50}$ values for ROCK 1 and ROCK 2 of 1.7 μM and 0.1 μM, respectively) than 23 (9 μM and 8 μM, respectively (FIG. 5). Similar results were also obtained with the 18/11 pair of analogs where treatment of MDA-MB-231 cells with 18 (10 μM) greatly decreased P-MLC2 levels whereas 11 at the same concentration did not. This is also consistent with the in vitro results where 18 inhibited more potently (IC$_{50}$ values of 0.65 μM and 0.67 μM) than 11 (IC$_{50}$ values of 157 μM and 62 μM) ROCK 1 and ROCK 2, respectively (FIG. 5). Furthermore, FIG. 4 also shows that the compounds were selective for decreasing the phosphorylation levels of the ROCK substrate MLC2 over the phosphorylation levels of Erk 1/2 proteins not known to be substrates for ROCK.

Methods

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation. Methods of treating inflammation in a subject are further provided herein, the methods comprising administering to the subject an effective amount of a compound or composition as described herein. Optionally, the methods can further include administering a second compound or composition (e.g., an anti-inflammatory agent).

The disclosed subject matter also concerns methods for treating a person or animal having a disorder or condition associated with aberrant or excessive ROCK activity or expression in a cell. In one embodiment, the disorder or condition is an oncological disorder or condition. In another embodiment, the disorder or condition is a cardiovascular-related disorder or condition. Examples of cardiovascular disorders and conditions that can be treated using the compounds and/or compositions disclosed herein include, but are not limited to, cerebral and coronary vasospasm, angina, hypertension, pulmonary hypertension, arteriosclerosis, ischemia/reperfusion injury, restenosis, stroke, and heart failure. In a further embodiment, the disorder or conition is a central nervous system (CNS) disorder or condition. Examples of CNS disorders and conditions that can be treated using the compounds and/or compositions disclosed herein include, but are not limited to, spinal cord injury, stroke, and Alzheimer's disease (AD). In one embodiment, a person or animal in need of treatment is administered an effective amount of one or more inhibitor compounds or compositions disclosed herein. In a specific embodiment, the compound is the compound designated herein as 8 through 27.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Means for administering and formulating compounds for administration to a patient are known in the art, examples of which are described herein. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lungcancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenstrom's macroglobulinemia, and Wilms' tumor.

Also disclosed are methods for inhibiting a ROCK protein in a cell by contacting the cell with an effective amount of a compound, agent, or composition disclosed herein. In one embodiment, the cell is a human or mammalian cell, and can be a cancer or tumor cell or other cell that exhibits abnormal proliferation, survival, migration or differentiation. In one embodiment, the cell constitutively expresses or expresses elevated or abnormal levels of a ROCK protein (e.g., ROCK1). In a specific embodiment, the compound is the compound designated herein as 8 through 27.

Also disclosed herein are methods for treating a person or animal having a disorder associated with constitutive, abnormal, or elevated expression of a ROCK protein in a cell, wherein a therapeutically effective amount of a compound, agent, or composition disclosed herein is administered to the person or animal. In many examples herein, the elevated ROCK protein expression is ROCK1. The disorder can be one characterized, for example, by abnormal cell proliferation, cell survival, cell migration, and/or cell differentiation. In a specific embodiment, the compound is the compound designated herein as 8 through 27.

Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that can benefit from the disclosed methods include fish, amphibians, avians, and reptiles. As used herein, the terms "patient" and "subject" are used interchangeably and are intended to include such human and non-human species. Likewise, in vitro methods disclosed herein can be carried out on cells of such human and non-human species.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane: sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. In one embodiment, compounds and compositions disclosed herein can be used in combination with other ROCK inhibitors, including, but not limited to, Y27632, Wf536, Fasudil, H-1152P, and CID5056270.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy*, 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Examples of some chemotherapeutic agents that can be used according to the disclosed methods are 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR Kits The disclosed subject matter also concerns a packaged dosage formulation comprising in one or more containers at least one inhibitor compound or composition disclosed herein, e.g., any compound of Formulas I through VIII. In one embodiment, a packaged dosage formulation comprises a compound designated herein as 8 through 27. A packaged dosage formulation can optionally comprise in one or more containers a pharmaceutically acceptable carrier or diluent. A packaged dosage formulation can also optionally comprise, in addition to an inhibitor compound or composition disclosed herein, other ROCK inhibitors, including, but not limited to, Y27632, Wf536, Fasudil, H-1152P, and/or CID5056270.

Depending upon the disorder or disease condition to be treated, a suitable dose(s) can be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form. A kit can also optionally comprise, in addition to an inhibitor compound or composition disclosed herein, other ROCK inhibitors, including, but not limited to, Y27632, Wf536, Fasudil, H-1152P, and/or CID5056270.

Alternative Synthesis of Pyridylthiazole Urea ROCK1 Inhibitors

The aminothiazole 5a was docked to the catalytic domain of ROCK1 (using GLIDE, and ROCK1 structure from pdb 2ESM) to determine a possible binding mode and to study the structural features responsible for binding of 5a to ROCK1. The model suggests that the pyridine ring binds to the hinge region via a hydrogen bond between the pyridyl nitrogen atom and the backbone amide NH of Met156 in a similar mode to the isoquinoline ring of Fasudil evident in its co-crystal complex with ROCK1 (Jacobs, et al., *J. Biol. Chem.*, 2006, 281:260-268). In the model, the carbonyl oxygen of 5a forms a hydrogen bond with the side chain NH of Lys-105 and the terminal phenyl ring of the benzylurea occupies a deep hydrophobic cleft under the P-Loop. The pyridylthiazole urea 5a inhibited ROCK1 ($IC_{50}$ 170 nM) and provided a new starting point. Attention was focused on exploring the SAR around the phenyl ring A, branching and substitution at the benzylic position, urea linkage of 5a, while retaining the hinge binding 4-(4-pyridinyl)-2-thiazolyl] group.

The compound 5a and additional analogs 5c, 5q, 5r, 5s, 5u and 5u, were prepared via microwave heating of aminothiazoles 7 or with isocyanates 9 following the synthetic route shown in Scheme 1. Microwave-assisted condensation of the commercially available 4-(bromoacetyl)pyridine (6) with thiourea and N-methylthiourea afforded the desired aminothiazoles 7 and 8, respectively. The aminothiazoles 7 and 8 were then reacted with commercially available isocyanates 9 to afford urea library 5 in poor to moderate yields. The initial SAR revealed the potential of the new urea analogs as a class of ROCK1 inhibitors.

An alternative synthetic route was then developed to improve the yields. Additionally, a significant drawback of the initial synthetic route was the lack of inexpensive commercially available isocyanates, which would limit the SAR around the benzyl group of compound 5a. The carbamate 10, prepared from the aminothiazole 7 and phenyl chloroformate provided a key intermediate and offered an alternative way to introduce significant chemical and structural diversity at the benzyl terminus of 5a via coupling with inexpensive and readily available benzylamines, amino acids, anilines, and aliphatic amines (Scheme 2). This proved to be successful, allowing library 5 to be expanded. As shown in Scheme 2, libraries 5 and 14 could be prepared by heating the reaction mixture in a sealed tube at 120° C. (Scheme 2, conditions b, g). By means of a heating block parallel station the generation of the library was performed in a combinatorial fashion. Moreover, microwave heating provided an efficient and convenient alternative to conventional heating for the synthesis of the desired library 5 (Scheme 2, conditions a, c-f). As a general note, longer reaction times or higher temperatures were required in the cases of less reactive amines. Diisopropylethylamine (DIPEA) or triethylamine were employed when the amine-containing reagents were available as the corresponding HCl salts (Scheme 2). To validate the new synthetic protocol, 5a and 5q were synthesized using the new synthetic route (Scheme 2). The different batches displayed comparable analytical data and comparable potency in the ROCK1 (FRET)-based Z'-Lyte kinase assay. Two compounds 12 and 13 were prepared to assess the effect of linker chain length. Finally, the corresponding mesylate and HCl salts of selected library members (5b, 5d and 5g) were also synthesized.

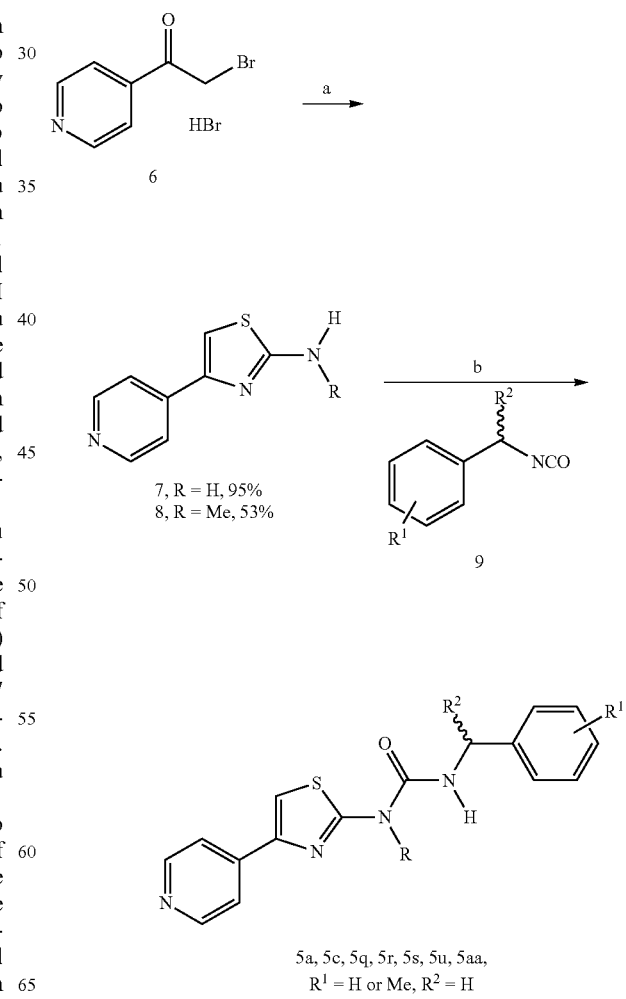

Scheme 1. First approach to the synthesis or ureas 5.

7, R = H, 95%
8, R = Me, 53%

5a, 5c, 5q, 5r, 5s, 5u, 5aa,
$R^1$ = H or Me, $R^2$ = H

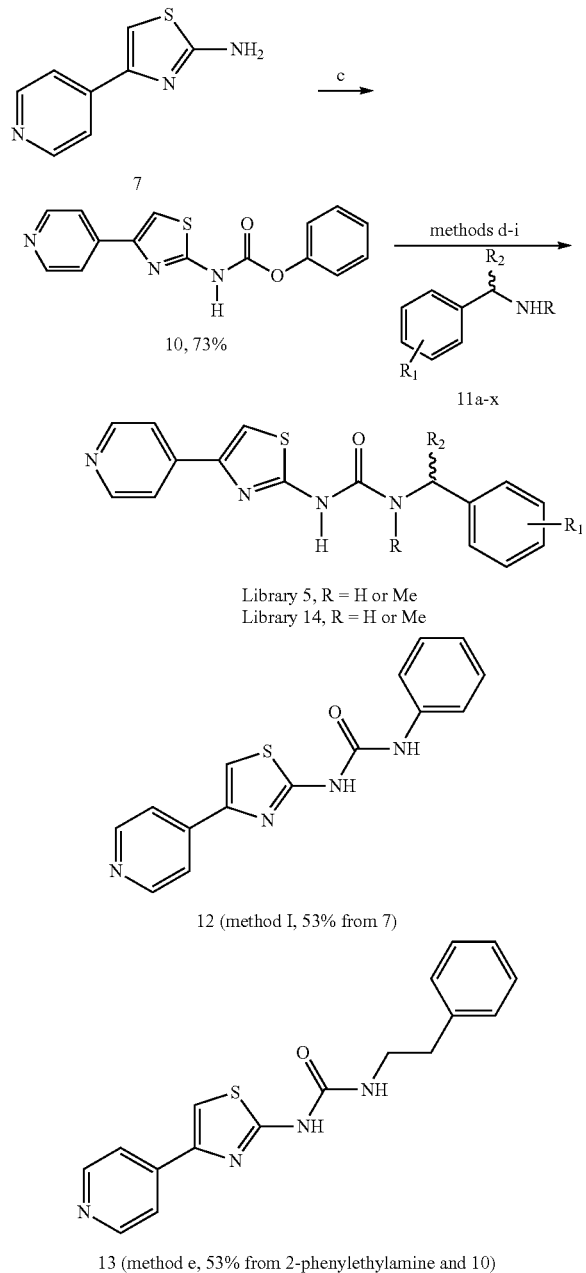

Scheme 2. Second route to urea libraries 5 and 14.

Library 5, R = H or Me
Library 14, R = H or Me 12 (method I, 53% from 7)

13 (method e, 53% from 2-phenylethylamine and 10)

Reagents & Conditions: c) Py, DCM, phenylchloroformate, rt, 3 h, Ar; d) THF, 112° C., sealed tube, heating block, 1 h; e) THF, 100° C., CEM microwave, 20 min; f) THF, DIPEA, 100° C., CEM microwave, 20 min; g) THF, Et$_3$N, 100° C. CEM microwave, 20 min; h) THF, CH$_3$CN, 80° C., Biotage microwave, 20 min; i) THF, 159° C., sealed tube, heating block, 4 h; THF, CEM microwave, 100° C., 10 min; k) DMF, CEM microwave, 150° C., 10 min; l) DMF, phenylisocyanate, Biotage microwave, 150° C., 10 min.

The structures of all the final compounds were confirmed by analysis of NMR and mass spectroscopic data. In addition, HPLC methods (typically two methods) were used to determine the purity (generally >96%) of the compounds. Additionally, HPLC methods were developed for the chiral compounds to determine the enantiomeric purity (generally >95%). All compounds were screened against ROCK1 and ROCK2. IC$_{50}$ values were systematically determined only for compounds that inhibited ROCK1 activity by at least 40% at a compound concentration of 50 μM.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process.

Materials and Methods

Reagents.

All chemicals and solvents were purchased from commercial suppliers and used without further purification. Preparative flash column chromatography was performed on silica gel, 0.040-0.063 mm (EMD Chemicals). $^1$H NMR (400 MHz) spectra were recorded on a Varian AS400 with a 60-place automated sample changer. High resolution ESI-MS spectra were recorded on an Agilent ESI-TOF L-MS 6200 system. Preparative HPLC was performed on a Gilson HPLC system with UV detectors and Gilson 215 liquid handler for auto injection and fraction collections (customized by HT Labs, San Diego). Analytical HPLC was performed on an Agilent 1100 series with diode array detectors and auto samplers. The specifications of HPLC analysis are as follows: flow rate, 1 mL/min; column, Intertsil, 2.5 μm, 4.6×150 mm; wavelength, 215, 254 and 280 nm; mobile phase, A: H$_2$O with 0.1% HCO$_2$H, B: MeOH, gradient of 30-95% B in 25 min. All tested compounds possessed a purity of not less than 95%.

Molecular Modeling.

Compound docking was carried out using the GLIDE, (Grid Based Ligand Docking from Energetics) program from Schrödinger, L.L.C. The Jorgensen OPLS-2005 force field was employed for GLIDE docking simulations. The optimal binding geometry (pose) for each modeled compound was obtained using GLIDE which employs Monte Carlo sampling techniques coupled with energy minimization. GLIDE also uses a scoring method based on ChemScore but with additional terms added to the scoring function for greater accuracy. GLIDE 5.7 SP (Standard Precision pMLC-2 pErk1/2 Tubulin DMSO 1 μM 10 μM 1 μM 10 μM 1 μM 10 μM 1 μM 10 μM 11 18 23 24 Total Erk1/2 Total MLC-2 S12 mode) was used to dock each chemical structure of these compounds followed by GLIDE 5.7 XP (Extra Precision mode) docking to find probable conformational hits. An X-ray crystal structure of human ROCK1 in complex with a small molecule inhibitor with fasudil at 3.20 Å resolution (2ESM.pdb) was used for ROCK 1 docking.

Kinase Assay.

A robust FRET-based, enzyme-coupled assay format, Z-Lyte® Kinase Assay Ser/Thr 13 Peptide Kit (Invitrogen, cat. PV3793), was employed in this study to monitor inhibition of ROCK1 (Invitrogen, cat. PV3691) and ROCK2

(Invitrogen, cat. PV3759) enzyme activities. Compounds were tested on three separate days with 8 point dilutions done in duplicate to determine the average $IC_{50}$ values. The assay conditions were optimized to 15 μl of kinase reaction volume with 5 ng of enzyme in 50 mM HEPES (pH 7.5), 10 mM $MgCl_2$, 1 mM EGTA, and 0.01% Brij-35. The reaction was incubated 1 hr. at room temperature in the presence of 1.5 μM of substrate with 12.5 μM of ATP (ROCK1 assay) or 2 μM of substrate with 50 μM of ATP (ROCK2 assay) in the presence of various concentrations of the compounds. The reaction was then stopped and the ratio of phosphorylated to unphosphorylated peptide substrate was determined by selective cleavage of only the unphosphorylated peptide as described by the manufacturer (Invitrogen, cat. PV3793). This was followed by excitation of coumarin at 400 nm resulting in emission at 445 nm and energy transfer to fluorescein and final emission at 520 nm. The substrate contains both coumarin and fluorescein and only uncleaved phosphorylated substrate will undergo FRET. $IC_{50}$ values were determined using fitted curves with GraphPad Prism 5 software. A known inhibitor, Y-27632 (Tocris Bioscience, cat. 1254), is used as a control compound.

Biochemical and Crystallographic Methods.

Reagents and compounds for biochemical and crystallographic experiments were purchased from Sigma-Aldrich (St. Louis, Mo.) and Hampton Research (Aliso Viejo, Calif.) unless otherwise indicated. The concentration of crystallization grade proteins was determined by A280 molar absorbance using a nanodrop ND-1000 spectrophotometer (Nanodrop Technologies).

Enzyme Purification.

The gene encoding the kinase domain of human ROCK1 (residues 6-415) was synthesized, cloned into the pFB-Dual-PBL bacmid to provide an N-terminal His-Puritin-tag, and expressed in SF9 insect cells after 72 h infection (Blue Sky Biotech, Worcester, Mass.). All purification steps were performed by FPLC at 4° C. Harvested insect cells were resuspended in 100 mM Na/K phosphate buffer (pH 7.4) containing 300 mM NaCl, 10 mM $MgCl_2$, 10 mM imidazole, 0.5 mg mL-1 lysosyme, and 0.01% Triton X-100 at 4° C. for 1 h. After sonication and centrifugation (1 h at 29000×g), the supernatant was purified by immobilized $Ni^{2+}$-ion affinity chromatography (GE LifeSciences, Piscataway, N.J.). Following incubation of peak fractions with TEV protease (20:1) at 4° C., the cleaved His-Puritin-tag was separated by size exclusion chromatography using a Superdex 75 (26/60) column, and eluted with 50 mM HEPES buffer (pH 7.4) containing 150 mM NaCl, 10 mM $MgCl_2$, 1 mM DTT. Purified ROCK1 (6-415) was buffer exchanged into 50 mM HEPES buffer (pH 7.4) containing 1 Mm DTT and concentrated to 20 mg mL-1 for crystallization.

Protein Crystallography.

Crystallization was performed at 18° C. using the sitting drop vapor diffusion method. Crystals of the ROCK1-18 complex were grown from 0.1 M HEPES pH 7.0, 5% tacsimate pH 7.0, and 10% PEG 5000 MME, in the presence of 1 mM inhibitor. Crystals were harvested in cryo-protectant mixture (reservoir solution including 25% (v/v) ethylene glycol and 1 mM inhibitor) and a complete data set was recorded at −180° C. at Beamline 22-ID, SER-CAT, Advanced Photon Source, Argonne National Laboratories from a single crystal. Data were reduced with S14 HKL2000 6. PHENIX 7 was employed for phasing and refinement, and model building was performed using Coot 8. Figures were prepared using PyMol (Schrödinger, LLC).

MYPT-1 in Intact Cancer Cells.

H1299 human lung cancer cells were treated for 1 hr with various ROCK inhibitors. The cells were then lysed and processed for western immunoblotting as described by us previously. The levels of phosphorylation of MYPT1 and total MYPT1 were determined by immunoblotting with the following antibodies: P-MYPT1 and total MYPT1 (Cell Signaling, Danvers, Ma).

Western Blot Analysis.

MDA-MB-468, MDA-MB-231, MCF-7, DU-145, H460, A549, HT29 and HCT116 cells (ATCC, Rockville, Md., USA) were plated in 6-well tissue culture plate. The cells were then treated next day with different concentrations of the RKIs for 1 h. After incubation, the cells were harvested, lysed, quantified and blotted for P-MLC2 (Cat no. 3671S), total-MLC2 (Cat no. 3672S), P-MEK (S298) (Cat no. 9128S), total-MEK (Cat no. 9122S), P-S6 (Cat no. 2155S), total-S6 (2217S), P-Erk (Cat no. 9101L), total Erk (Cat no. 9102L), P-Akt (Cat no. 9271L), total Akt (Cat no. 9272L) (Cell Signaling, Danvers, Mass., USA) and tubulin (Cat no. 5168) (Sigma, St Louis, Mo., USA) antibodies as described by us previously Cell Morphology Assay.

NIH 3T3 cells were plated at 8000 cells per well in 8-chamber slide in serum-free media (serum starvation) for 24 h. After serum starvation, the cells were treated with vehicle or the RKIs for 1 h. After treatment, the cells were stimulated with 10 mM LPA, 200 ng/ml bradykinin or 30 ng/ml PDGF for 30 min. After stimulation, the cells were fixed with 4% paraformaldehyde, permeabilized using 0.1% Triton X-100 and stained with Texas-Red phalloidin (Cat no. T7471) (Invitrogen, Eugene, Oreg., USA) and DAPI (40,6 diamidino-2-phenylindole: counterstains DNA) (Cat no. H-1200; Vector Laboratories, Burlingame, Calif., USA). The cells were imaged using Zeiss Upright Fluorescence Microscope.

Soft Agar Assay.

MDA-MB-231 cells were seeded in a 12-well tissue culture plate at 1200 cells per well in regular growth media and 0.3% agar. The cells were treated with different doses of RKI-11 and RKI-18, allowed to grow for 4 weeks, after which the colonies were stained overnight with 1 mg/ml MTT and counted.

MTT Assay.

MTT assay was performed to determine the effects of RKIs on anchoragedependent cell proliferation. Briefly, cells were plated in a 96-well tissue culture plate (1200 cells per well) and incubated for 24 h. After incubation, the cells were treated with vehicle or increasing concentrations of RKI-11 or RKI-18 (0.05-50 mM). After 72 h incubation, freshly prepared MTT (2 mg/ml) was added to each well and incubated for 3 h. After incubation, the plates were read at 540 nm.

Wound-Healing-Migration Assay.

MDA-MB-231 cells were seeded at 4_105 cells per well in a 6-well plate and allowed to grow overnight at 37 1 C and 5% $CO_2$. The cells were starved for 24 h and scratched. The cells were then treated with different concentrations of RKIs in regular growth media for 24 h. Images of the scratch were acquired at 0 h and 24 h.

Invasion Assay.

Invasion assay was performed in Corning Transwell inserts coated with Matrigel. MDA-MB-231 cells were seeded at 3.5_105 and allowed to grow overnight in a 6-well plate. The cells were treated with either vehicle or different doses of RKIs for 24 h. After treatment, the cells were trypsinized, resuspended and plated in the inserts. The bottom chamber contained 20% FBS as the 'chemoattractant'. The cells were kept in the incubator for 48 h. After incubation, the cells were stained and membrane was quantified.

Synthetic Procedure for Compounds 1-7.

A mixture of 4-aminopyridine (47 mg, 0.5 mmol), picolinic acid (62 mg, 0.5 mmol) and N-ethyl-N'-(3-dimethylaminopropyl)carbodiimide (192 mg, 1 mmol) in DMF (2 mL) was stirred at room temperature overnight. After solvent was removed under reduced pressure, the residue was purified by flash column chromatography (hexane:ethyl acetate, 1:1). The product 1 (74 mg) was obtained in 74% yield. The same procedure was used to synthesize 2 (99 mg, 99%), 3 (95 mg, 95%), 4 (reaction on 1.0 mmol scale, 136 mg, 58%) and 5 (reaction on 2.0 mmol scale, 514 mg, 92%). Compounds 6 and 7 were prepared using a general procedure as follows: A mixture of 4 (23 mg, 0.1 mmol), 4-fluorophenylboronic acid (21 mg, 0.15 mmol), Pd(PPh$_3$)$_4$ (36 mg, 0.03 mmol) and K$_2$CO$_3$ (21 mg, 0.15 mmol) in dioxane-H$_2$O (4:1, 2 mL) was heated at 95° C. for 16 hr. After solvent was removed under reduced pressure, the residue was purified by flash column chromatography (hexane:ethyl acetate, 1:3). Compound 6 (20 mg) was obtained in 72% yield. Compound 7 (27 mg, 97%) was obtained from 5.

N-(Pyridin-4-yl)picolinamide (1)

$^1$H NMR (400 MHz, d$_6$-DMSO) δ 11.04 (s, 1H), 8.78 (d, J=4.7 Hz, 1H), 8.50 (dd, J=4.8, 1.5 Hz, 2H), 8.19 (d, J=7.8 Hz, 1H), 8.10 (td, J=7.7, 1.7 Hz, 1H), 7.96 (dd, J=4.8, 1.6 Hz, 2H), 7.73 (ddd, J=7.5, 4.8, 1.2 Hz, 1H); MS (ESI) m/z=200 [M+H]$^+$; HPLC purity, 99.8%.

N-(pyridin-4-yl)isonicotinamide (2)

$^1$H NMR (400 MHz, d$_6$-DMSO) δ 10.85 (s, 1H), 8.82 (dd, J=4.4, 1.6 Hz, 2H), 8.52 (d, J=6.3 Hz, 2H), 7.87 (dd, J=4.4, 1.7 Hz, 2H), 7.78 (dd, J=4.8, 1.6 Hz, 2H); MS (ESI) m/z=200 [M+H]$^+$; HPLC purity, 99.4%.

N-(Pyridin-4-yl)nicotinamide (3)

$^1$H NMR (400 MHz, d$_6$-DMSO) δ 10.80 (s, 1H), 9.12 (d, J=1.6 Hz, 1H), 8.80 (dd, J=4.8, 1.6 Hz, 1H), 8.51 (dd, J=4.8, 1.6 Hz, 2H), 8.34-8.27 (m, 1H), 7.78 (dd, J=4.8, 1.6 Hz, 2H), 7.60 (dd, J=8.0, 4.8 Hz, 1H); MS (ESI) m/z=200 [M+H]$^+$; HPLC purity, 99.6%.

4-Chloro-N-(pyridin-4-yl)nicotinamide (4)

$^1$H NMR (400 MHz, d$_6$-DMSO) δ 11.08 (s, 1H), 8.80 (s, 1H), 8.66 (d, J=5.4 Hz, 1H), 8.49 (dd, J=4.9, 1.6 Hz, 2H), 7.71 (d, J=5.4 Hz, 1H), 7.65 (d, J=6.3 Hz, 2H); MS (ESI) m/z=234 [M+H]$^+$; HPLC purity, 99.6%.

5-Bromo-N-(pyridin-4-yl)nicotinamide (5)

$^1$H NMR (400 MHz, d$_6$-DMSO) δ 10.82 (s, 1H), 9.05 (d, J=1.8 Hz, 1H), 8.93 (d, J=2.2 Hz, 1H), 8.54 (t, J=2.1 Hz, 1H), 8.50-8.48 (m, 2H), 7.75-7.71 (m, 2H); MS (ESI) m/z=278 [M+H]$^+$; HPLC purity, 99.0%.

4-(4-Fluorophenyl)-N-(pyridin-4-yl)nicotinamide (6)

$^1$H NMR (400 MHz, d$_6$-DMSO) δ 10.92 (s, 1H), 8.81 (s, 1H), 8.77 (d, J=5.1 Hz, 1H), 8.44 (d, J=4.9 Hz, 2H), 7.60-7.45 (m, 5H), 7.30 (t, J=8.8 Hz, 2H); MS (ESI) m/z=294 [M+H]$^+$; HPLC purity, 96.0%.

5-(4-Fluorophenyl)-N-(pyridin-4-yl)nicotinamide (7)

$^1$H NMR (400 MHz, d$_6$-DMSO) δ 10.83 (s, 1H), 9.06 (dd, J=15.0, 2.1 Hz, 2H), 8.52 (dd, J=5.8, 3.7 Hz, 3H), 7.91-7.84 (m, 2H), 7.79-7.66 (m, 2H), 7.43-7.29 (m, 2H); MS (ESI) m/z=294 [M+H]$^+$; HPLC purity, 95.1%.

Synthetic Procedure for Compounds 9-19.

To a mixture of 1H-indazol-5-amine (240 mg, 1.8 mmol) and pyridine (3 mL) in DCM (3 mL) was added phenyl chloroformate (283 mg, 1.8 mmol) at 0° C. The mixture was warmed to room temperature and stirred for 3 hr. After DCM and pyridine were removed under reduced pressure, the residue was purified by flash column chromatography (DCM:MeOH, 20:1). Compound 9 (360 mg) was obtained in 80% yield. A mixture of 9 (35 mg, 0.14 mmol), dimethylamine (70 μL of 2.0 M in THF, 0.14 mmol) and DIPEA (36 mg, 0.28 mmol) in DMF (1 mL) was heated at 90° C. for 14 hr. After solvent was removed under reduced pressure, the residue was purified by flash column chromatography (DCM:MeOH, 20:1). Compound 10 (22 mg) was obtained in 77% yield. Using the same procedure, compound 11 (10 mg, 50%) was obtained from 9 and aniline. Compound 12 (36 mg, 90%) from 9 and benzylamine. Compound 13 (40 mg, 97%) from 9 and N-methyl-2-phenylethanamine. Compound 14 (33 mg, 80%) from 9 and (S)-2-amino-3-phenylpropan-1-ol. Compound 15 (25 mg, 60%) from 9 and 2-amino-1-phenylethanol. Compound 16 (35 mg, 81%) from 9 and 2-(4-methoxyphenyl)ethanamine. Compound 17 (28 mg, 64%) from 9 and 2-(4-chlorophenyl)ethanamine. Compound 18 (30 mg, 89%) from 9 and 2-phenylethanamine.

Phenyl 1H-indazol-5-ylcarbamate (9)

$^1$H NMR (400 MHz, CD$_3$OD) δ 7.97 (d, J=9.7 Hz, 2H), 7.38-7.51 (m, 4H), 7.15-7.26 (m, 3H); MS (ESI) m/z=254 [M+H]$^+$.

3-(1H-Indazol-5-yl)-1,1-dimethylurea (10)

$^1$H NMR (400 MHz, CD$_3$OD) δ 7.95 (s, 1H), 7.69 (d, J=1.1 Hz, 1H), 7.43 (d, J=8.9 Hz, 1H), 7.36 (dd, J=8.9 Hz, 1.7 Hz, 1H), 3.01 (s, 6H); MS (ESI) m/z 205 [M+H]$^+$; HRMS (ESI) calcd for C$_{10}$H$_{13}$N$_4$O, 205.1084. found 205.1156. HPLC purity, 98.3%.

1-(1H-Indazol-5-yl)-3-phenylurea (11)

$^1$H NMR (400 MHz, d$_6$-DMSO) δ 12.91 (s, 1H), 8.61 (d, J=6.2 Hz, 2H), 7.97 (s, 1H), 7.89 (s, 1H), 7.45 (m, 3H), 7.27 (m, 3H), 6.74 (t, J=7.3 Hz, 1H); MS (ESI) m/z 253 [M+H]$^+$; HRMS (ESI) calcd for C$_{14}$H$_{13}$N$_4$O: 253.1084. found 253.1084. HPLC purity, 95.8%

1-Benzyl-3-(1H-indazol-5-yl)urea (12)

$^1$H NMR (400 MHz, d$_6$-DMSO) δ, 12.84 (s, 1H), 8.47 (s, 1H), 7.92 (s, 1H), 7.84 (s, 1H), 7.34 (m, 5H), 7.24 (m, 2H), 6.53 (t, J=5.9 Hz, 1H), 4.29 (d, J=5.9 Hz, 2H); MS (ESI) m/z=267 [M+H]$^+$; HRMS (ESI) calcd for C$_{15}$H$_{15}$N$_4$O, 267.1240. found 267.1255. HPLC purity, 95.1%

3-(1H-Indazol-5-yl)-1-methyl-1-phenethylurea (13)

$^1$H NMR (400 MHz, CD$_3$OD) δ 7.95 (s, 1H), 7.63 (d, J=1.3 Hz, 1H), 7.43 (d, J=8.9 Hz, 1H), 7.27 (m, 5H), 7.19

(m, 1H), 6.03 (t, J=5.6 Hz, 1H), 3.61 (t, J=7.3 Hz, 2H), 2.95 (s, 3H), 2.89 (t, J=7.4 Hz, 2H); MS (ESI) m/z 295 [M+H]$^+$; HRMS (ESI) calcd for $C_{17}H_{19}N_4O$, 295.1553. found 295.1610. HPLC purity, 96.6%.

(S)-1-(1-Hydroxy-3-phenylpropan-2-yl)-3-(1H-indazol-5-yl)urea (14)

$^1$H NMR (400 MHz, d$_6$-DMSO) δ 12.83 (s, 1H), 8.42 (s, 1H), 7.90 (s, 1H), 7.80 (d, J=1.3 Hz, 1H), 7.37 (d, J=8.9 Hz, 1H), 7.26 (m, 4H), 7.17 (m, 2H), 6.01 (d, J=8.3 Hz, 1H), 4.90 (t, J=5.2 Hz, 1H), 3.82 (m, 1H), 3.32 (m, 2H), 2.82 (dd, J=13.6 Hz, 6.6 Hz, 1H), 2.69 (dd, J=13.5 Hz, 7.3 Hz, 1H); MS (ESI) m/z 311 [M+H]$^+$; HRMS (ESI) calcd for $C_{17}H_{19}N_4O_2$ 311.1503. found 311.1612. HPLC purity, 98.1%.

1-(2-Hydroxy-2-phenylethyl)-3-(1H-indazol-5-yl)urea (15)

$^1$H NMR (400 MHz, d$_6$-DMSO) δ 12.85 (s, 1H), 8.55 (s, 1H), 7.91 (s, 1H), 7.81 (d, J=1.1 Hz, 1H), 7.35 (m, 5H), 7.22 (m, 2H), 6.14 (t, J=6.0 Hz, 1H), 5.59 (d, J=4.3 Hz, 1H), 4.61 (m, 1H), 3.36 (m, 1H), 3.11 (m, 1H); MS (ESI) m/z 297 [M+H]$^+$; HRMS (ESI) calcd for $C_{16}H_{17}N_4O_2$ 297.1346. found 297.1424. HPLC purity, 98.9%.

1-(1H-Indazol-5-yl)-3-(4-methoxyphenethyl)urea (16)

$^1$H NMR (400 MHz, d$_6$-DMSO) δ 12.84 (s, 1H), 8.39 (s, 1H), 7.91 (s, 1H), 7.81 (d, J=1.5 Hz, 1H), 7.37 (d, J=8.8 Hz, 1H), 7.20 (dd, J=8.9 Hz, 1.8 Hz, 1H), 7.14 (m, 2H), 6.86 (m, 2H), 6.00 (t, J=5.6 Hz, 1H), 3.70 (s, 3H), 3.27 (m, 2H), 2.66 (t, J=6.9 Hz, 2H); MS (ESI) m/z 311 [M+H]$^+$; HRMS (ESI) calcd for $C_{17}H_{19}N_4O_2$ 311.1503. found 311.1562. HPLC purity, 95.1%.

1-(4-Chlorophenethyl)-3-(1H-indazol-5-yl)urea (17)

$^1$H NMR (400 MHz, d$_6$-DMSO) δ 12.84 (s, 1H), 8.38 (s, 1H), 7.91 (s, 1H), 7.81 (d, J=1.4 Hz, 1H), 7.36 (m, 3H), 7.25 (m, 2H), 7.20 (dd, J=8.8 Hz, 1.8 Hz, 1H), 6.03 (t, J=5.7 Hz, 1H), 3.31 (m, 2H), 2.73 (t, J=7.0 Hz, 1H); MS (ESI) m/z 315 [M+H]$^+$; HRMS (ESI) calcd for $C_{16}H_{16}ClN_4O$, 315.1007. found 315.1010. HPLC purity, 95.4%.

1-(1H-Indazol-5-yl)-3-phenethylurea (18)

$^1$H NMR (400 MHz, d$_6$-DMSO) δ 12.83 (s, 1H), 8.40 (s, 1H), 7.91 (s, 1H), 7.82 (d, J=1.4 Hz, 1H), 7.37 (d, J=8.8 Hz, 1H), 7.29 (m, 2H), 7.20 (m, 4H), 6.03 S7 (t, J=5.6 Hz, 1H), 3.37 (m, 2H), 3.73 (t, J=7.2 Hz, 2H); MS (ESI) m/z 281 [M+H]$^+$; HRMS (ESI) calcd for $C_{16}H_{17}N_4O$, 281.1397. found 281.1424. HPLC purity, 97.4%.

1-(1H-indazol-5-yl)-3-(3-phenylpropyl)urea (19)

$^1$H NMR (400 MHz, d$_6$-DMSO) δ 12.83 (s, 1H), 8.34 (s, 1H), 7.91 (s, 1H), 7.82 (d, J=1.5 Hz, 1H), 7.38 (d, J=8.9 Hz, 1H), 7.25 (m, 5H), 7.14 (m, 1H), 6.13 (t, J=5.6 Hz, 1H), 3.08 (m, 2H), 2.59 (t, J=7.5 Hz, 2H), 1.72 (p, J=7.4 Hz, 2H); MS (ESI) m/z 295 [M+H]$^+$; HRMS (ESI) Calcd for $C_{17}H_{19}N_4O$: 295.1553. Found: 295.1604. HPLC purity, 98.7%.

Synthetic Procedure for Synthesis of 20-27

4-(Pyridin-4-yl)aniline (20) was prepared in three steps: To a mixture of 4-bromoaniline (950 mg, 5.6 mmol), triethylamine (678 mg, 6.7 mmol) and DMAP (73 mg, 0.56 mmol) in DCM (30 mL) was added Boc$_2$O (1.22 g, 5.6 mmol) at 0° C. The reaction mixture was allowed to warm to room temperature and stirred for 2 hr. After the reaction was quenched with 5% NaHCO$_3$, the mixture was extracted with DCM (3×20 mL). The organic layer was combined and dried over anhydrous MgSO$_4$. tert-Butyl 4-bromophenylcarbamate (1.36 g, 90%) was obtained after flash column chromatography (hexane: ethyl acetate, 4:1). Suzuki coupling reaction of tert-butyl 4-bromophenylcarbamate (800 mg, 2.95 mmol) with 4-pyridineboronic acid (300 mg, 2.46 mmol) in the presence of Pd(PPh$_3$)$_4$ (57 mg, 0.05 mmol) and K$_2$CO$_3$ (678 mg, 4.9 mmol) in dioxane-H$_2$O (4:1, 10 mL) at 90° C. for 14 hr. tert-Butyl 4-(pyridin-4-yl)phenylcarbamate (600 mg, 75%) was obtained after flash column chromatography (DCM:MeOH, 20:1). Compound 20 (380 mg, 99%) was obtained after treatment of tert-butyl 4-(pyridin-4-yl)phenylcarbamate (600 mg, 2.2 mmol) with DCM:TFA (1:1, 1 mL) for 2 hr at room temperature followed by solvent removal. To a mixture of 4-(pyridin-4-yl)aniline 20 (380 mg, 2.24 mmol) and pyridine (3 mL) in DCM (3 mL) was added phenyl chloroformate (366 mg, 2.35 mmol) at 0° C. The mixture was allowed to warm to room temperature and stirred for 3 hr. After DCM and pyridine were removed under reduced pressure, the residue was purified by flash column chromatography (DCM:MeOH, 20:1). Compound 21 (400 mg) was obtained in 65% yield. A mixture of 21 (22 mg, 0.08 mmol), benzylamine (9.8 mg, 0.09 mmol) in DMSO (0.6 mL) was heated at 90° C. for 14 hr. After solvent was removed under reduced pressure, the residue was purified by flash column chromatography (DCM:MeOH, 20:1) to afford compound 22 (18 mg, 78%). Using the same procedure, compound 23 (12 mg, 47%) was obtained from 21 and (R)-2-amino-2-phenylethanol, compound 24 (12 mg, 47%) from 21 and (S)-2-amino-2-phenylethanol, compound 25 (20 mg, 83%) from 21 and 2-phenylethanamine, compound 26 (25 mg, 90%) from 21 and (R)-2-amino-3-phenylpropan-1-ol, and compound 26 (12 mg, 45%) from 21 and (S)-2-amino-3-phenylpropan-1-ol.

4-(Pyridin-4-yl)aniline (20)

$^1$H NMR (400 MHz, d$_6$-DMSO) δ 8.81 (s, 2H), 8.25 (s, 2H), 7.76 (d, J=8.7 Hz, 2H), 6.87 (m, 2H), 2.09 (s, 2H); MS (ESI) m/z 171 [M+H]$^+$; HRMS (ESI) calcd for $C_{11}H_{11}N_2$ 171.0917. found 171.0938.

Phenyl 4-(pyridin-4-yl)phenylcarbamate (21)

$^1$H NMR (400 MHz, d$_6$-DMSO) δ 9.59 (s, 1H), 8.96 (s, 2H), 8.28 (s, 2H), 8.03 (m, 2H), 7.87 (m, 2H), 7.46 (m, 2H), 7.26 (m, 3H); MS (ESI) m/z 291 [M+H]$^+$; HRMS (ESI) calcd for $C_{18}H_{15}N_2O_2$ 291.1128. found 291.1142.

1-Benzyl-3-(4-(pyridin-4-yl)phenyl)urea (22)

$^1$H NMR (400 MHz, d$_6$-DMSO) δ 8.58 (s, 2H), 8.28 (s, 1H), 7.68 (m, 4H), 7.62 (m, 2H), 7.34 (m, 4H), 7.24 (m, 1H), 6.33 (t, J=4.9 Hz, 1H), 4.43 (d, J=5.9 Hz, 2H); MS (ESI) m/z 304 [M+H]$^+$; HRMS (ESI) calcd for $C_{19}H_{18}N_{13}O$, 304.1444. found 304.1479. HPLC purity, 96.2%.

(R)-1-(2-Hydroxy-1-phenylethyl)-3-(4-(pyridin-4-yl)phenyl)urea (23)

$^1$H NMR (400 MHz, CD$_3$OD) δ 8.52 (d, J=6.1 Hz, 2H), 7.69 (m, 4H), 7.53 (d, J=8.7 Hz, 2H), 7.37 (m, 4H), 7.26 (t,

J=6.8 Hz, 1H), 3.82 (m, 1H), 3.73 (m, 1H); MS (ESI) m/z 334 [M+H]$^+$; HRMS (ESI) calcd for $C_{20}H_{20}N_3O_2$ 334.1550. found 334.1577. HPLC purity, 95.6%.

(S)-1-(2-Hydroxy-1-phenylethyl)-3-(4-(pyridin-4-yl)phenyl)urea (24)

$^1$H NMR (400 MHz, d$_6$-DMSO) δ 8.88 (s, 1H), 8.53 (d, J=5.4 Hz, 2H), 7.69 (d, J=8.6 Hz, 2H), 7.63 (d, J=5.9 Hz, 2H), 7.49 (d, J=8.7 Hz, 2H), 7.31 (m, 4H), 7.22 (m, 1H), 6.78 (d, J=7.8 Hz, 1H), 5.02 (t, J=5.1 Hz, 1H), S94.74 (m, 1H), 3.63 (m, 1H), 3.56 (m, 1H); MS (ESI) m/z 334 [M+H]$^+$; HRMS (ESI) calcd for $C_{20}H_{20}N_3O_2$ 334.1550. found 334.1576; HPLC purity, 95.3%.

1-Phenethyl-3-(4-(pyridin-4-yl)phenyl)urea (25)

$^1$H NMR (400 MHz, d$_6$-DMSO) δ 8.58 (d, J=4.0 Hz, 2H), 8.19 (s, 1H), 7.67 (m, 4H), 7.62 (m, 2H), 7.28 (m, 4H), 7.21 (m, 1H), 5.88 (s, 1H), 3.48 (m, 2H), 2.84 (t, J=7.3 Hz, 2H); MS (ESI) m/z 318 [M+H]$^+$; HRMS (ESI) calcd for $C_{20}H_{20}N_3O$, 318.1601. found 318.1626. HPLC purity, 96.4%.

(R)-1-(1-Hydroxy-3-phenylpropan-2-yl)-3-(4-(pyridin-4-yl)phenyl)urea (26)

$^1$H NMR (400 MHz, CD$_3$OD) δ 8.51 (s, 2H), 7.68 (m, 4H), 7.48 (m, 2H), 7.29 (m, 4H), 7.20 (m, 1H), 4.03 (m, 1H), 3.57 (m, 2H), 2.94 (m, 1H), 2.82 (m, 1H); MS (ESI) m/z 348 [M+H]$^+$; HRMS (ESI) calcd for $C_{21}H_{22}N_3O_2$ 348.1707. found 348.1712. HPLC purity, 95.9%.

(S)-1-(1-Hydroxy-3-phenylpropan-2-yl)-3-(4-(pyridin-4-yl)phenyl)urea (27)

$^1$H NMR (400 MHz, CD$_3$OD) δ 8.51 (dd, J=4.9 Hz, 1.3 Hz, 2H), 7.68 (m, 4H), 7.47 (m, 2H), 7.28 (m, 4H), 7.20 (m, 1H), 4.02 (m, 1H), 3.56 (dd, J=4.7 Hz, 2.2 Hz, 2H), 2.87 (m, 2H); MS (ESI) m/z 348 [M+H]$^+$; HRMS (ESI) calcd for $C_{21}H_{22}N_3O_2$ 348.1707. found 348.1732; HPLC purity, 95.2%.

Effects of ROCK Inhibitors on the Phosphorylation Levels of MLC2 (a ROCK Substrate) and Erk1/2 (not a ROCK Substrate) in Human Cancer Cells.

MDA-MB-231 breast cancer cells were treated for 1 hr with two pairs of compounds 23/24 (24 is active in vitro and its stereoisomer 23 is less active and 11/18 (18 is active in vitro whereas its analog 11 is much less active). The cells were then lysed and processed for western immunoblotting as described by us previously. The levels of phosphorylation of MLC2, Erk1/2, total MLC2, total Erk1/2 and total Tubulin were determined by immunoblotting with the following antibodies: P-MLC2, P-Erk1/2, total MLC2 and total Erk1/2 (Cell Signaling, Danvers, Ma) and total Tubulin (Sigma, Saint Louis, Mo.).

The in vitro kinase SAR yielded potent and selective ROCK inhibitors. It was next determined that some of these are capable of entering intact cells, reaching their target and inhibiting ROCK from phosphorylating its substrate MLC2. To this end, human breast cancer MDAMB-231 cells were treated for 1 h with 2 pairs of compounds 23/24 and 11/18 representing two classes of the disclosed inhibitors and processed the cells for determining the levels of phosphorylation of MLC2 (PMLC2). FIG. 4 shows that treatment of the breast cancer cells with 24 at 1 and 10 μM greatly decreased P-MLC2 levels, whereas its stereoisomer 23 had no effect at 1 μM and was less potent than 24 at 10 μM. This is consistent with the in vitro kinase studies where 24 was more potent (IC$_{50}$ values for ROCK 1 and ROCK 2 of 1.7 and 0.1 μM, respectively) than 23 (9 and 8 μM, respectively). Similar results were also obtained with the 18/11 pair of analogues where treatment of MDA-MB-231 cells with 18 (10 μM) greatly decreased PMLC2 levels, whereas 11 at the same concentration did not. This is also consistent with the in vitro results where 18 inhibited more potently (IC$_{50}$ values of 0.65 and 0.67 μM) than 11 (IC$_{50}$ values of 157 and 62 μM) ROCK 1 and ROCK 2, respectively (FIG. 5). Furthermore, FIG. 4 also shows that the compounds were selective for decreasing the phosphorylation levels of the ROCK substrate MLC2 over the phosphorylation levels of Erk 1/2 proteins not known to be substrates for ROCK.
Potential Hydrogen Bonding Interactions in the Hinge with 18 (a) and 22 (b).

Crystallization was performed at 18° C. using the sitting drop vapor diffusion method. Crystals of the ROCK1 with compound 18 complex were grown from 0.1 M HEPES (pH 7.0), 5% tacsimate (pH 7.0), and 10% PEG 5000 MME, in the presence of 1 mM inhibitor. Crystals were harvested in cryo-protectant mixture (reservoir solution including 25% (v/v) ethylene glycol and 1 mM inhibitor) and a complete data set was recorded at −180° C. at Beamline 22-ID, SER-CAT, Advanced Photon Source, Argonne National Laboratories from a single crystal. Data were reduced with S14 HKL2000 6. PHENIX 7 was employed for phasing and refinement, and model building was performed using Coot 8. Figures were prepared using PyMol (Schrödinger, LLC). The atomic coordinates and structure factor for ROCK1 in complex with compound 18 have been deposited under accession number 3V8S.

These studies identified ROCK inhibitors as therapies for pathological conditions such as glaucoma. Optimization of fragments yielded potent (100 nM) ROCK inhibitors that inhibited in intact human cancer cells at low micromolar concentration the phosphorylation of MLC2, a ROCK substrate but not the phosphorylation of proteins that are not substrates of ROCK such as Erk1/2.

Identification of a Pair of Closely Related Structural Analogs RKI-18 (Potent) and RKI-11 (Weak/Inactive) ROCK Inhibitors The effects of these inhibitors on signaling, anchorage-dependent and -independent tumor cell growth, apoptosis, migration and invasion were investigated by selecting a pair of closely related analogs, one potent and the other weak/inactive inhibitors. 18 and 11 are structurally very close indazole urea-based analogs where in 18 the indazole urea and the phenyl group are linked by the two carbon ethylene, whereas in 11 they are attached directly without a linker (FIG. 5). FIG. 5 shows that 18 and 11 inhibited ROCK1 with IC$_{50}$ values of 397 nM and 38 mM. FIG. 5 also shows that 18 and 11 inhibited ROCK2 with IC$_{50}$ values of 349 nM and 45 mM, respectively. Thus, 18 was 96- to 129-fold more potent than 11, providing an ideal pair of potent/weak (inactive) chemical probes for investigating the effects of ROCK inhibition on malignant transformation.

Figure 6:
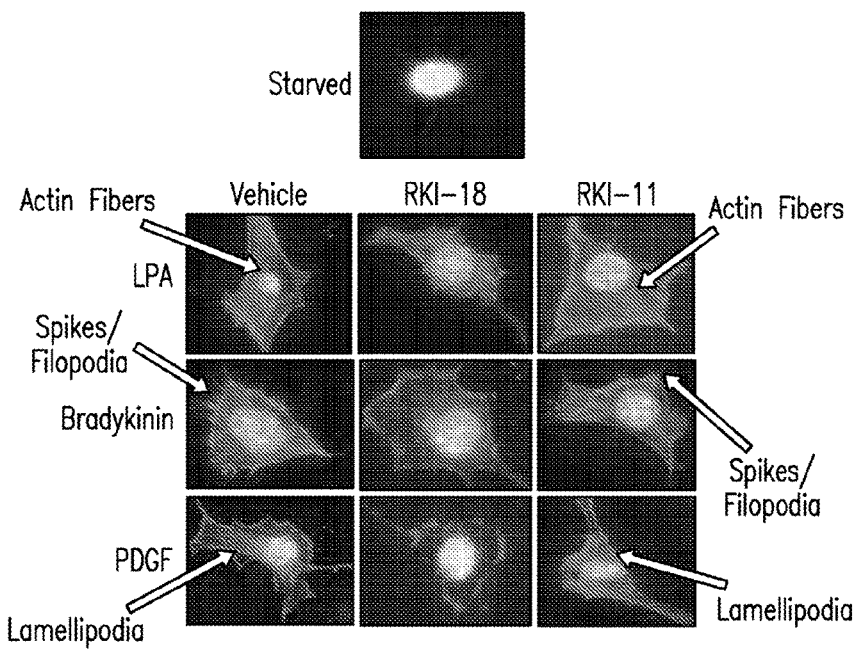
FIG. 6 shown that RKI-18 but not RKI-11 inhibits the formation of stress fibers, filopodia and lamellipodia upon stimulation with LPA, bradykinin and PDGF, respectively. Starved NIH 3T3 cells were treated with either vehicle or RKIs (10 mM) for 1 h before treatment with either LPA, bradykinin or PDGF. The cells were then fixed and stained with Texas-Red phalloidin and DAPI as described in Materials and methods. Data are representative of three independent experiments.

RKI 18 but not RKI-11 Inhibits LPA-, Bradykinin- and PDGF-Induced Stress Fiber Formation, Filopodia and Lamelipodia, Respectively Stress fiber formation upon stimulation with LPA (lysophosphatidic acid) is a cytoskeleton re-organization process mediated by the activation of RhoA/ROCK pathway, whereas PDGF stimulation of lamelipodia formation is mediated by the RAC1/PAK pathway, and bradykinin stimulation of filopodia (spikes) formation is mediated by the CDC42/PAK pathway. To determine the effects of the disclosed inhibitors on these morphological changes, NIH 3T3 cells were starved and treated with either 11, 18 or vehicle prior to stimulating them with either LPA, PDGF or bradykinin, and then staining the cells with phalloidin. FIG. 6 shows that RKI-18 but not RKI-11 inhibited LPA-induced stress fiber formation, bradykinin-induced filopodia formation and PDGF-induced lamelipodia formation (FIG. 6). The ability of 18 to inhibit the formation of actin stress fiber, filopodia and lamelipodia, cytoskeletal changes that are critical to cell motility, suggests that this inhibitor may interfere with the ability of cancer cells to migrate and invade.

Figure 7A:
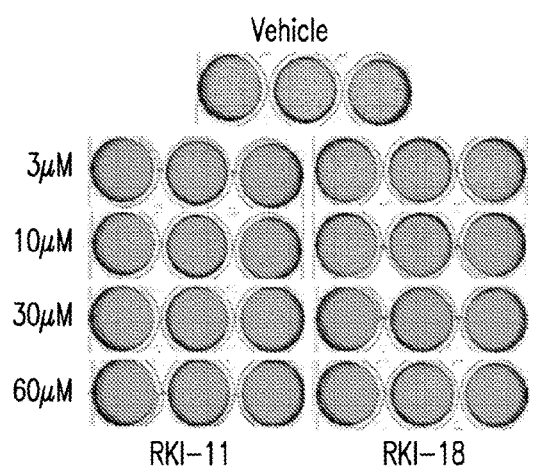
FIGS. 7A-7C: RKI-18 but not RKI-11 inhibits anchorage-independent growth of human breast cancer cells. MDA-MB-231 cells were treated with various concentrations of RKIs (3 mM, 10 mM, 30 mM and 60 mM) and processed for anchorage-independent soft agar growth (FIGS. 7A and 7B) as described under Materials and methods section (data show the average of two independent experiments).
Figure 7B:
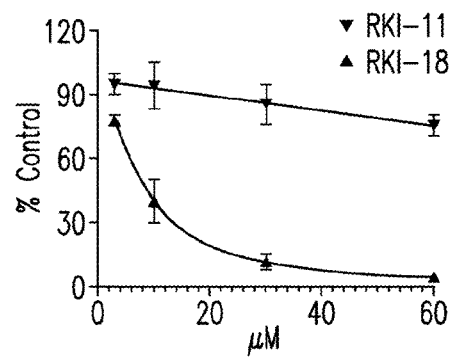
Figure 7C:
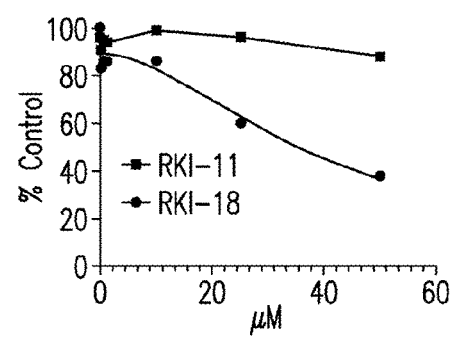

RKI-18 but not RKI-11 Inhibits Anchorage-Independent Growth, Migration and Invasion of Human Breast Cancer Cells The ability of cancer cells to metastasize depends on their ability to grow in an anchorage-independent manner, migrate and invade. The effects of 18 and 11 to affect these cancer hallmarks were investigated. To this end, the ability of these compounds to inhibit anchorage-independent growth in soft agar assay was first determined. The results from FIG. 7A and FIG. 7B demonstrate that 18 inhibited soft agar colony formation of MDA-MB-231 cells with an $IC_{50}$ of 8 mM, whereas the closely related analog and less active ROCK inhibitor 11 had little effect at 60 mM on anchorage independent growth. To determine the effects of 18 and 11 on anchorage-dependent proliferation and survival, MDA-MB-231 cells were treated with increasing concentrations of the inhibitors and processed for MTT assays as well as western blotting. FIG. 7C shows that RKI-18 was four-fold less potent at inhibiting anchorage-dependent proliferation ($IC_{50}$⅓32 mM) as compared to anchorage-independent growth ($IC_{50}$⅓8 mM). Furthermore, 18 treatment (up to 30 mM) of these cells did not induce apoptosis as measured by caspase 3 activation and PARP cleavage. These results evidence that the ability of 18 to inhibit the anchorage-independent growth of cancer cell on soft agar is not due to inhibition of anchorage-dependent proliferation and/or induction of apoptosis.

Figure 8A:
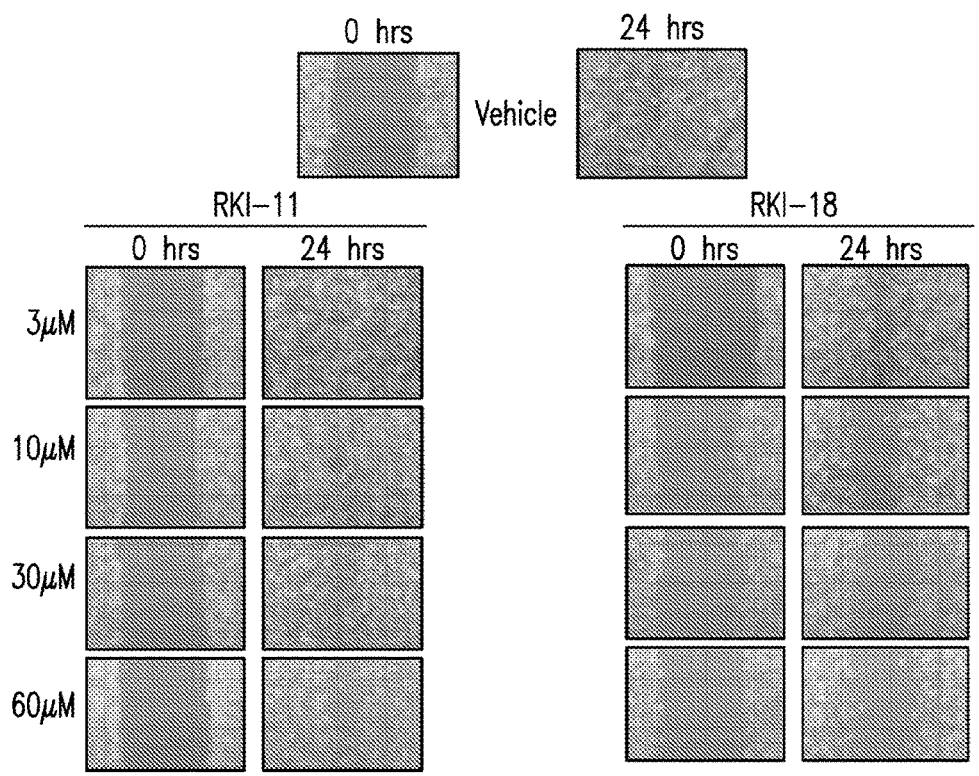
FIGS. 8A and 8B show RKI-18 but not RKI-11 inhibits migration and invasion of human breast cancer cells.
Figure 8B:
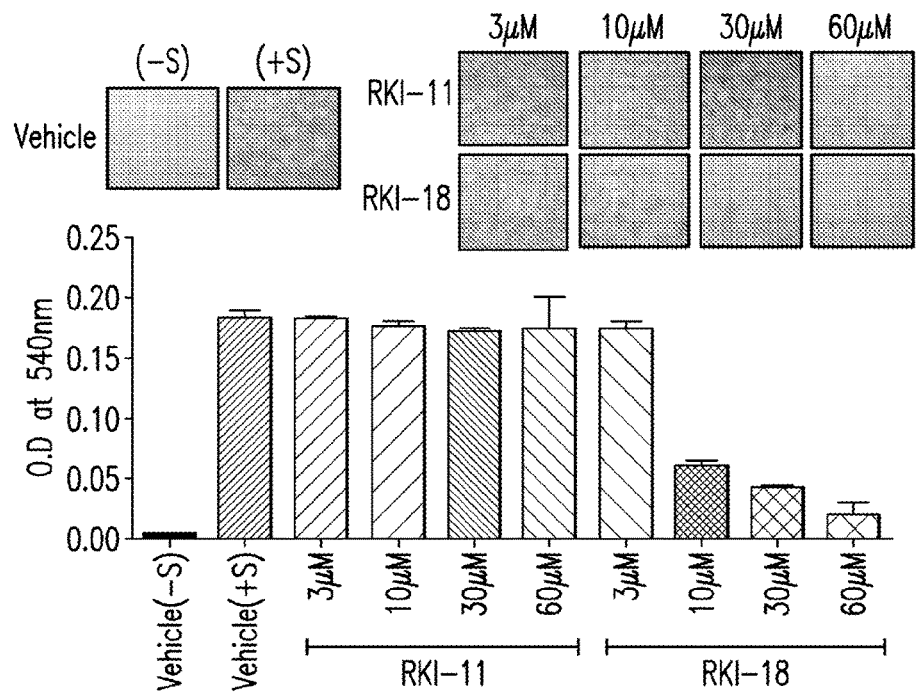

The ability of these compounds to inhibit migration of breast cancer cells in a wound-healing scratch assay was determined. 18 inhibited the migration of MDA-MB-231 cells in a concentration-dependent manner starting at 3 mM (FIG. 8A). In contrast, RKI-11 at 60 mM did not inhibit the migration of these cells (FIG. 8A). The ability of cancer cells to metastasize depends on their ability to invade; we therefore, investigated the ability of RKIs to inhibit invasion. FIG. 8B shows that 18 at 10 mM inhibited the cancer cells from invading through Matrigel by 67%, whereas 11 had no effect on cell invasion at 60 mM.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A method of reducing or inhibiting tumor growth in a subject with breast cancer, comprising: administering to the subject an effective amount of a composition comprising a compound having the chemical structure shown in Formula IV

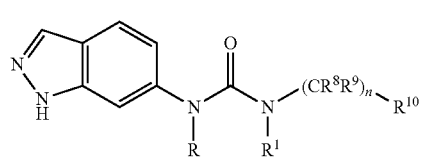

wherein
R is H, alkyl, acetyl, or heteroalkyl;
$R^1$ is H, alkyl, acetyl, or heteroalkyl;
$R^8$ and $R^9$ are, independently of one another, H, —OH, acetyl, —C(O)NH$_2$, alkyl, cycloalkyl, hereterocycloalkyl, aryl, or heteroaryl, wherein any one of the alkyl, cycloalkyl, hereterocycloalkyl, aryl, or heteroaryl groups is optionally substituted with one or more of —OH, —NO$_2$, —NH$_2$, —NR$^6$R$^7$, carbonyl, alkoxy, alkyl, —OCX$_3$, —OCHX$_2$, —OCH$_2$X, or halogen, or both $R^8$ together form a carbonyl; and
$R^{10}$ is cycloalkyl, aryl, or heteroaryl, any of which is optionally substituted with one or more of —OH, —C(O)NH$_2$, —C(O)CH$_3$, —NO$_2$, —NH$_2$, —NR$^6$R$^7$, carbonyl, alkyl, alkoxy, alkylalkoxy, alkoxylalkoxy, halogenated alkoxyl, cycloalkyl, heterocycloalkyl, heteroarylcarbonyl, aryl, heteroaryl, —OCX$_3$, —OCHX$_2$, —OCH$_2$X, —OSO$_2$CH$_3$, or -tosyl;
$R^6$ and $R^7$ are, independently, H, alkyl, —SO$_2$CH$_3$, —C(O)CH$_3$, or —C(O)NH$_2$;
X is independently H or halogen; and
n is 2 or 3,
or a pharmaceutically acceptable salt thereof.

2. The method of claim 1, wherein n is 2.

3. The method of claim 1, wherein $R^8$ and $R^9$ are, independently, H, alkyl, or alkyl substituted with —OH, —NH$_2$, alkoxy, or halogen.

4. The method of claim 1, wherein $R^{10}$ is an aryl or heteroaryl, any of which is optionally substituted in the ortho-, meta-, or para-position with —OH, —CO$_2$CH$_3$, —C(O)NH$_2$, —NO$_2$, —NH$_2$, —NR$^6$R$^7$, alkoxy, alkylalkoxy, alkyl, —OSO$_2$CH$_3$, or tosyl.

5. The method of claim 1, wherein the compound has the formula

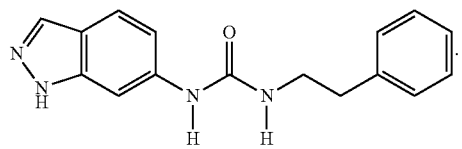 [SMILES: O=C(NCCc1ccccc1)Nc1ccc2cn[nH]c2c1]

6. The method of claim 1, wherein the cancer is breast cancer.

7. The method of claim 1, further comprising administering a second anticancer agent or an anti-inflammatory agent to the subject.

8. The method of claim 1, further comprising administering Y27632, Wf536, Fasudil, H-1152P, and/or CID5056270 to the subject.

9. The method of claim 1, further comprising administering an effective amount of ionizing radiation to the subject.

10. A method of reducing or inhibiting tumor growth in a subject with breast cancer, comprising: administering to the subject an effective amount of a composition comprising a compound having the chemical structure shown in Formula I

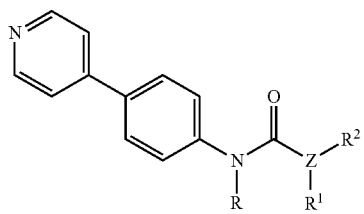

wherein
Z is CR or N;
R is H, alkyl, acetyl, or heteroalkyl;
$R^1$ is H, alkyl, acetyl, or heteroalkyl;
$R^2$ is alkyl, cycloalkyl, heterocycloalkyl, aryl, heteroaryl, or alkylaryl, any of which can be optionally substituted with one or more of —OH, —$CH_2OH$, —$C(O)NH_2$, acetyl, carbonyl, alkyl, cycloalkyl, heterocycloalkyl, aryl, or heteroaryl, any of which can be optionally substituted with one or more of —OH, —$NO_2$, —$NH_2$, —$NR^6R^7$, alkyl, alkoxy, alkylalkoxy, alkoxylalkoxy, halogenated alkoxy, heteroarylcarbonyl, heteroaryl, —$OCX_3$, —$OCHX_2$, —$OCH_2X$, —$OSO_2CH_3$, tosyl, or halogen; or
$R^1$ and $R^2$ can together form a cycloalkyl or heterocycloalkyl
$R^6$ and $R^7$ are, independently, H, alkyl, —$SO_2CH_3$, —$C(O)CH_3$, or —$C(O)NH_2$;
X is independently H or halogen;
with the proviso that R and $R^1$ are not both H when $R^2$ is $CH(CH_2OH)Ph$;
or a pharmaceutically acceptable salt or hydrate thereof.

11. The method of claim 10, wherein the compound has the chemical structure shown in Formula III

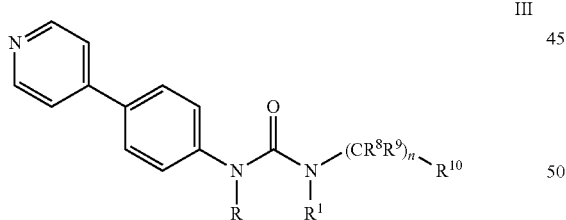

wherein
$R^8$ and $R^9$ are, independently of one another, H, —OH, acetyl, —$C(O)NH_2$, alkyl, cycloalkyl, hereterocycloalkyl, aryl, or heteroaryl, wherein any one of the alkyl, cycloalkyl, hereterocycloalkyl, aryl, or heteroaryl groups is optionally substituted with one or more of —OH, —$NO_2$, —$NH_2$, —$NR^6R^7$, carbonyl, alkoxy, alkyl, —$OCX_3$, —$OCHX_2$, —$OCH_2X$, or halogen, or both $R^8$ together form a carbonyl; and
$R^{10}$ is cycloalkyl, heterocycloalkyl, aryl, or heteroaryl, any of which is optionally substituted with one or more of —OH, —$C(O)NH_2$, —$C(O)CH_3$, —$NO_2$, —$NH_2$, —$NR^6R^7$, carbonyl, alkyl, alkoxy, alkylalkoxy, alkoxylalkoxy, halogenated alkoxyl, cycloalkyl, heterocycloalkyl, heteroarylcarbonyl, aryl, heteroaryl, —$OCX_3$, —$OCHX_2$, —$OCH_2X$, —$OSO_2CH_3$, -tosyl, or halogen; and
n is 1, 2, or 3.

12. The method of claim 10, wherein n is 1 or 2.

13. The method of claim 10, wherein $R^8$ and $R^9$ are, independently, H, alkyl, or alkyl substituted with —OH, —$NH_2$, alkoxy, or halogen.

14. The method of claim 10, wherein n is 1, and $CR^8R^9$ is the R isomer of CHalkyl, wherein the alkyl group is substituted with —OH, $NH_2$, alkoxy, or halogen.

15. The method of claim 10, wherein n is 1, and $CR^8R^9$ is the S isomer of CHalkyl, wherein the alkyl group is substituted with —OH, $NH_2$, alkoxy, or halogen.

16. The method of claim 10, wherein $R^{10}$ is an aryl or heteroaryl, any of which is optionally substituted in the ortho-, meta-, or para-position with —OH, —$CO_2CH_3$, —$C(O)NH_2$, —$NO_2$, —$NH_2$, —$NR^6R^7$, alkoxy, alkylalkoxy, alkyl, —$OSO_2CH_3$, tosyl, or halogen.

17. The method of claim 10, wherein $(CR^8R^9)_nR^{10}$ have the combined structure:

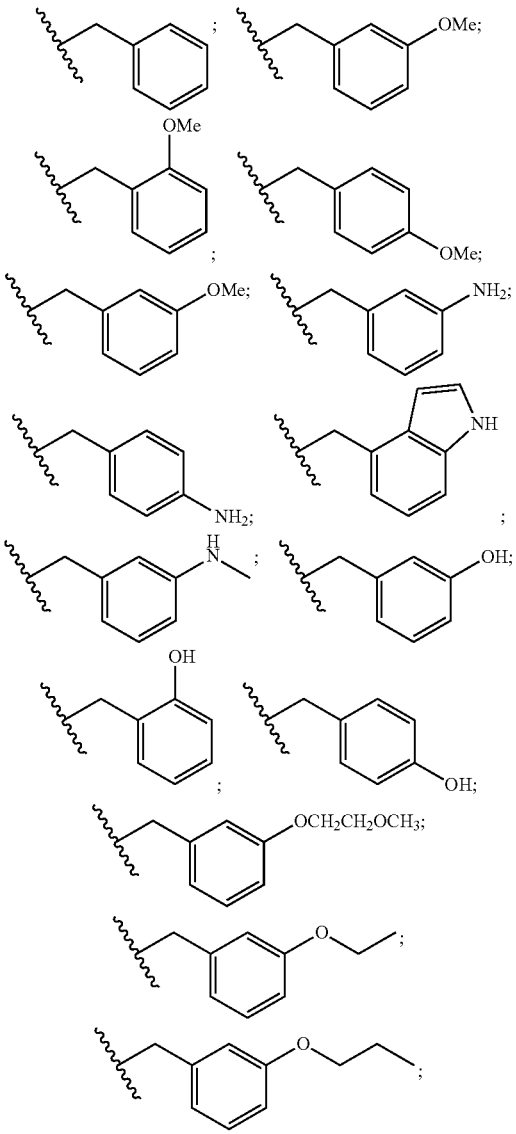

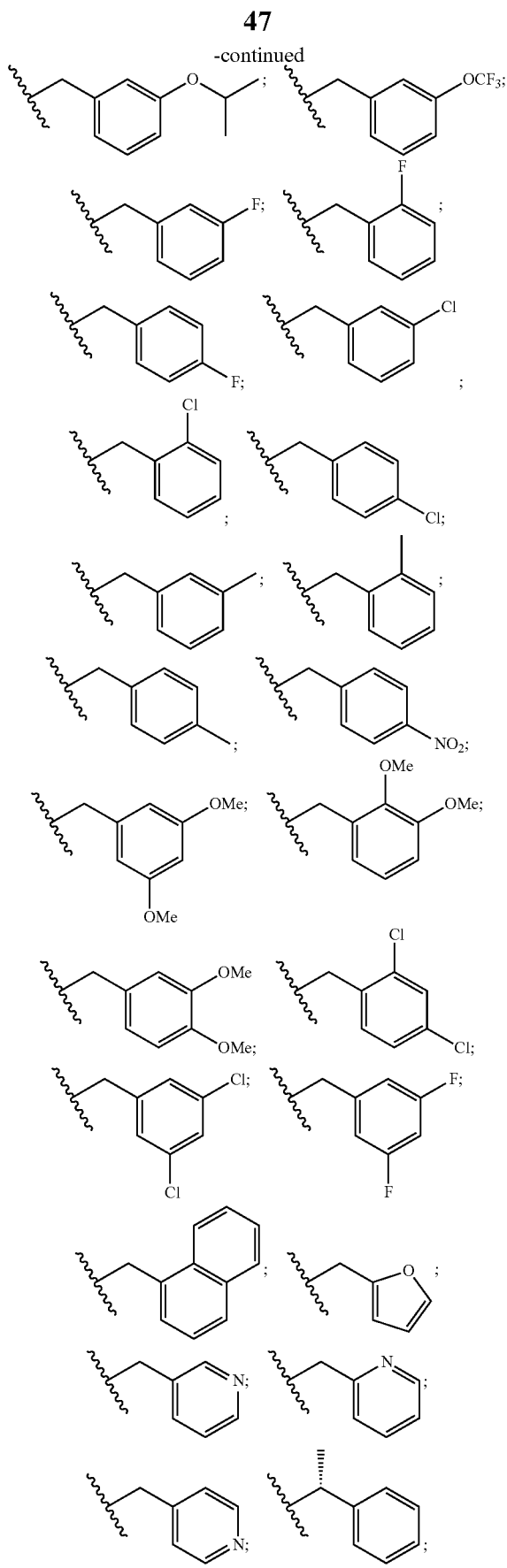

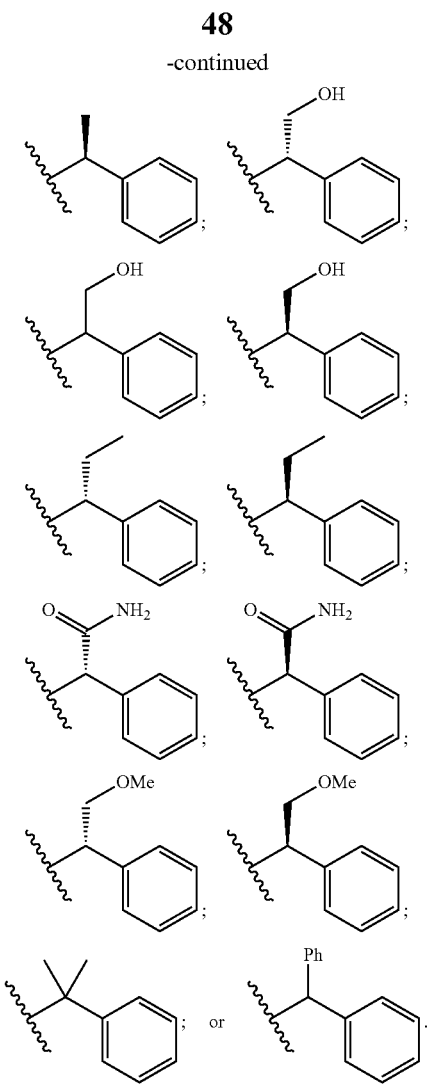

18. The method of claim 10, where the compound is

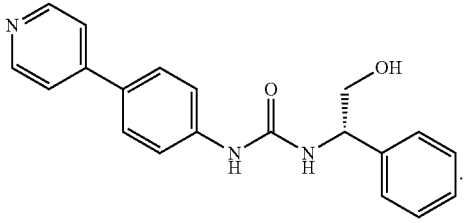 [SMILES: O=C(Nc1ccc(-c2ccncc2)cc1)N[C@H](CO)c1ccccc1]

19. The method of claim 10, further comprising administering a second anticancer agent or an anti-inflammatory agent to the subject.

20. The method of claim 10, further comprising administering Y27632, Wf536, Fasudil, H-1152P, and/or CID5056270 to the subject.

21. The method of claim 10, further comprising administering an effective amount of ionizing radiation to the subject.

* * * * *